United States Patent
Lohmueller

(10) Patent No.: US 11,117,936 B2
(45) Date of Patent: Sep. 14, 2021

(54) AFFINITY-ENHANCED MONOMERIC STREPTAVIDIN CHIMERIC ANTIGEN RECEPTOR (CAR)

(71) Applicant: University of Pittsburgh—Of the Commonwealth System of Higher Education, Pittsburgh, PA (US)

(72) Inventor: Jason Lohmueller, Pittsburgh, PA (US)

(73) Assignee: University of Pittsburg—Of the Commonwealth System of Higher Education, Pittsburgh, PA (US)

( * ) Notice: Subject to any disclaimer, the term of this patent is extended or adjusted under 35 U.S.C. 154(b) by 61 days.

(21) Appl. No.: 16/183,579

(22) Filed: Nov. 7, 2018

(65) Prior Publication Data
US 2019/0161520 A1 May 30, 2019

Related U.S. Application Data

(60) Provisional application No. 62/584,601, filed on Nov. 10, 2017.

(51) Int. Cl.
| | | |
|---|---|---|
| *A61K 35/17* | (2015.01) | |
| *C07K 14/36* | (2006.01) | |
| *C07K 14/705* | (2006.01) | |
| *C07K 14/725* | (2006.01) | |
| *A61P 35/00* | (2006.01) | |
| *A61P 35/02* | (2006.01) | |
| *C07K 16/28* | (2006.01) | |
| *A61K 39/00* | (2006.01) | |
| *A61K 38/00* | (2006.01) | |
| *C07K 16/30* | (2006.01) | |

(52) U.S. Cl.
CPC ............ *C07K 14/36* (2013.01); *A61K 35/17* (2013.01); *A61K 39/0011* (2013.01); *A61P 35/00* (2018.01); *A61P 35/02* (2018.01); *C07K 14/7051* (2013.01); *C07K 14/70517* (2013.01); *C07K 14/70521* (2013.01); *C07K 14/70578* (2013.01); *C07K 16/2803* (2013.01); *A61K 38/00* (2013.01); *A61K 2039/5156* (2013.01); *C07K 16/2863* (2013.01); *C07K 16/2887* (2013.01); *C07K 16/3092* (2013.01); *C07K 2317/24* (2013.01); *C07K 2317/622* (2013.01); *C07K 2317/73* (2013.01); *C07K 2319/02* (2013.01); *C07K 2319/03* (2013.01); *C07K 2319/20* (2013.01); *C07K 2319/30* (2013.01); *C07K 2319/33* (2013.01)

(58) Field of Classification Search
CPC ............ A61K 35/17; A61K 2039/5156; A61K 2039/6006; A61K 2039/625; C07K 2319/33; C07K 2319/70; C07K 2318/20
USPC ........................................................ 424/133.1
See application file for complete search history.

(56) References Cited

U.S. PATENT DOCUMENTS

| | | |
|---|---|---|
| 9,233,125 B2 | 1/2016 | Davila et al. |
| 9,561,291 B2 | 2/2017 | Kovesdi et al. |
| 9,624,276 B2 | 4/2017 | Young et al. |

FOREIGN PATENT DOCUMENTS

| | | |
|---|---|---|
| WO | WO 2010/129265 A3 | 11/2010 |
| WO | WO 2013/044225 A1 | 9/2012 |

OTHER PUBLICATIONS

Lohmueller et al (Oncoimmunology Oct. 26, 2017;7(1):e1368604. doi: 10.1080/2162402X.2017.1368604).*
Lehtolainen etal (Gene Therapy (2003) 10, 2090-2097).*
Lim et al., "Stable, high-affinity streptavidin monomer for protein labeling and monovalent biotin detection," *Biotechnology Bioeng.* 110: 57-67 (2013).
Lohmueller et al., "msa2 biotin-binding CAR combined with biotinylated tumor-specific antibodies or DNA aptamers for "universal" cancer immunotherapy," *AACR Annual Meeting*, Poster Presentation (Apr. 4, 2017).
Ma et al., Versatile strategy for controlling the specificity and activity of engineered T cells, *PNAS* 113(4): E450-E458 (e-pub Jan. 12, 2016).
Tamada et al., "Redirecting gene-modified T cells toward various cancer types using tagged antibodies," *Clin. Cancer Res.* 18: 6436-6445 (e-pub Oct. 2, 2012).
Urbanska et al., "A universal strategy for adoptive immunotherapy of cancer through use of a novel T cell antigen receptor," *Cancer Res.* 72(7): 1844-1852, Apr. 1, 2012.

* cited by examiner

*Primary Examiner* — Lynn A Bristol
(74) *Attorney, Agent, or Firm* — Klarquist Sparkman, LLP

(57) ABSTRACT

A chimeric antigen receptor is disclosed that includes: (a) an extracellular high affinity streptavidin;(b) a hinge domain from CD8; (c) a CD28 transmembrane domain; (d) an intracellular 4-1BB and/or CD28 signaling domain; and (e) an intracellular CD3 zeta signaling domain, wherein (a)-(e) are in N-terminal to C-terminal order. Nucleic acids encoding this chimeric antigen receptor, and T and natural killer (NK) cells transformed with this chimeric antigen receptor are also disclosed. The use of this chimeric antigen receptor for the treatment of tumors is also disclosed.

20 Claims, 13 Drawing Sheets

Specification includes a Sequence Listing.

FIG. 7A

| msa2-CD28ζ CAR DNA sequence |
|---|
| ATGGAGACAGACACACTCCTGCTATGGGTGCTGCTGCTCTGGGTTCCAGGTTCCAC
AGGTGGCGCAGAGGCGGGTATCACCGGGACATGGTACAACCAACACGGAAGC
ACATTTACAGTCACCGCTGGAGCAGACGGGAATCTGACCGGACAGTACGAGA
ACAGGGCTCAGGGGACAGGTTGTCAGAACAGTCCGTATACTCTGACTGGGAG
GTACAATGGCACGAAGCTGGAGTGGCGAGTCGAGTGGAATAATTCCACGGAA
AACTGTCACAGTAGAACAGAGTGGAGGGGACAGTACCAGGGGGGAGCAGAG
GCCCGGATCAACACCCAATGGAACTTGACATATGAAGGCGGGTCAGGCCCCG
CGACAGAGCAAGGACAGGATACATTCACGAAGGTCAAGCCAAGCGCAGCCTC
TGGCTCTACCACAACTCCAGCTCCCCGGCCCCCTACTCCTGCTCCAACCATTGCCT
CACAGCCACTGAGCCTGCGGCCCGAAGCTTGTAGACCTGCTGCTGGAGGAGCTGT
GCATACCAGAGGCCTGGACTTCGCCTGCGAT*ATGTTCTGGGTGCTGGTGGTGGTGGG
CGGGGTGCTGGCCTGCTACAGCCTGCTGGTGACAGTGGCCTTCATCATCTTTTGGGTGC
GGAGCAAGCGGAGCAGAGGCGGCCACAGCGACTACATGAACATGACCCCCAGACGGC
CTGGCCCCACCCGGAAGCACTACCAGCCCTACGCCCCACCCAGGGACTTTGCCGCCTA
CCGGTCCGGCGGAGGGCGGGT*GAAGTTCAGCAGAAGCGCCGACGCCCCTGCCTAC
CAGCAGGGCCAGAATCAGCTGTACAACGAGCTGAACCTGGGCAGAAGGGAAGAG
TACGACGTCCTGGATAAGCGGAGAGGCCGGGACCCTGAGATGGGCGGCAAGCCTC
GGCGGAAGAACCCCCAGGAAGGCCTGTATAACGAACTGCAGAAAGACAAGATGG
CCGAGGCCTACAGCGAGATCGGCATGAAGGGCGAGCGGAGGCGGGGCAAGGGCC
ACGACGGCCTGTATCAGGGCCTGTCCACCGCCACCAAGGATACCTACGACGCCCT
GCACATGCAGGCCCTGCCCCCAAGGCTCGAGGGCGGCGGAGAGGGCAGAGGAAG
TCTTCTAACATGCGGTGACGTGGAGGAGAATCCCGGCCCTCGCATGAGCGAGCTG
ATTAAGGAGAACATGCACATGAAGCTGTACATGGAGGGCACCGTGGACAACCATC
ACTTCAAGTGCACATCCGAGGGCGAAGGCAAGCCCTACGAGGGCACCCAGACCAT
GAGAATCAAGGTGGTCGAGGGCGGCCCTCTCCCCTTCGCCTTCGACATCCTGGCTA
CTAGCTTCCTCTACGGCAGCAAGACCTTCATCAACCACACCCAGGGCATCCCCGAC
TTCTTCAAGCAGTCCTTCCCTGAGGGCTTCACATGGGAGAGAGTCACCACATACGA
AGACGGGGGCGTGCTGACCGCTACCCAGGACACCAGCCTCCAGGACGGCTGCCTC
ATCTACAACGTCAAGATCAGAGGGGTGAACTTCACATCCAACGGCCCTGTGATGC
AGAAGAAAACACTCGGCTGGGAGGCCTTCACCGAGACGCTGTACCCCGCTGACGG
CGGCCTGGAAGGCAGAAACGACATGGCCCTGAAGCTCGTGGGCGGGAGCCATCTG
ATCGCAAACATCAAGACCACATATAGATCCAAGAAACCCGCTAAGAACCTCAAGA
TGCCTGGCGTCTACTATGTGGACTACAGACTGGAAAGAATCAAGGAGGCCAACAA
CGAAACATACGTCGAGCAGCACGAGGTGGCAGTGGCCAGATACTGCGACCTCCCT
AGCAAACTGGGGCACAAGCTTAATTAA |

FIG. 7B

| msa2-41BBζ CAR DNA sequence |
|---|
| ATGGAGACAGACACACTCCTGCTATGGGTGCTGCTGCTCTGGGTTCCAGGTTCCAC
AGGTGGCGCAGAGGCGGGTATCACCGGGACATGGTACAACCAACACGGAAGC
ACATTTACAGTCACCGCTGGAGCAGACGGGAATCTGACCGGACAGTACGAGA
ACAGGGCTCAGGGACAGGTTGTCAGAACAGTCCGTATACTCTGACTGGGAG
GTACAATGGCACGAAGCTGGAGTGGCGAGTCGAGTGGAATAATTCCACGGAA
AACTGTCACAGTAGAACAGAGTGGAGGGGACAGTACCAGGGGGGAGCAGAG
GCCCGGATCAACACCCAATGGAACTTGACATATGAAGGCGGGTCAGGCCCCG
CGACAGAGCAAGGACAGGATACATTCACGAAGGTCAAGCCAAGCGCAGCCTC
TGGCTCTACCACAACTCCAGCTCCCCGGCCCCCTACTCCTGCTCCAACCATTGCCT
CACAGCCACTGAGCCTGCGGCCCGAAGCTTGTAGACCTGCTGCTGGAGGAGCTGT
GCATACCAGAGGCCTGGACTTCGCCTGCGAT*ATGTTCTGGGTGCTGGTGGTGGG*
*CGGGGTGCTGGCCTGCTACAGCCTGCTGGTGACAGTGGCCTTCATCATCTTTTGGGTG*A
AACGGGGCAGAAAGAAACTCCTGTATATATTCAAACAACCATTTATGAGACCAGT
ACAAACTACTCAAGAGGAAGATGGCTGTAGCTGCCGATTTCCAGAAGAAGAAGA
AGGAGGATGTGAACTGCGGGTGAAGTTCAGCAGAAGCGCCGACGCCCCTGCCTAC
CAGCAGGGCCAGAATCAGCTGTACAACGAGCTGAACCTGGGCAGAAGGGAAGAG
TACGACGTCCTGGATAAGCGGAGAGGCCGGGACCCTGAGATGGGCGGCAAGCCTC
GGCGGAAGAACCCCAGGAAGGCCTGTATAACGAACTGCAGAAAGACAAGATGG
CCGAGGCCTACAGCGAGATCGGCATGAAGGGCGAGCGGAGGCGGGGCAAGGGCC
ACGACGGCCTGTATCAGGGCCTGTCCACCGCCACCAAGGATACCTACGACGCCCT
GCACATGCAGGCCCTGCCCCCAAGGCTCGAGGGCGGCGGAGAGGGCAGAGGAAG
TCTTCTAACATGCGGTGACGTGGAGGAGAATCCCGGCCCTCGCATGAGCGAGCTG
ATTAAGGAGAACATGCACATGAAGCTGTACATGGAGGGCACCGTGGACAACCATC
ACTTCAAGTGCACATCCGAGGGCGAAGGCAAGCCCTACGAGGGCACCCAGACCAT
GAGAATCAAGGTGGTCGAGGGCGGCCCTCTCCCCTTCGCCTTCGACATCCTGGCTA
CTAGCTTCCTCTACGGCAGCAAGACCTTCATCAACCACACCCAGGGCATCCCCGAC
TTCTTCAAGCAGTCCTTCCCTGAGGGCTTCACATGGGAGAGAGTCACCACATACGA
AGACGGGGGCGTGCTGACCGCTACCCAGGACACCAGCCTCCAGGACGGCTGCCTC
ATCTACAACGTCAAGATCAGAGGGGTGAACTTCACATCCAACGGCCCTGTGATGC
AGAAGAAAACACTCGGCTGGGAGGCCTTCACCGAGACGCTGTACCCCGCTGACGG
CGGCCTGGAAGGCAGAAACGACATGGCCCTGAAGCTCGTGGGCGGGAGCCATCTG
ATCGCAAACATCAAGACCACATATAGATCCAAGAAACCCGCTAAGAACCTCAAGA
TGCCTGGCGTCTACTATGTGGACTACAGACTGGAAAGAATCAAGGAGGCCAACAA
CGAAACATACGTCGAGCAGCACGAGGTGGCAGTGGCCAGATACTGCGACCTCCCT
AGCAAACTGGGGCACAAGCTTAATTAA |

FIG. 7C

| FMC63-CD28ζ CAR DNA sequence |
|---|
| ATGGAGACAGACACACTCCTGCTATGGGTGCTGCTGCTCTGGGTTCCAGGTTCCAC |
| AGGTGACATCCAGATGACACAGACTACATCCTCCCTGTCTGCCTCTCTGGGAG |
| ACAGAGTCACCATCAGTTGCAGGGCAAGTCAGGACATTAGTAAATATTTAAAT |
| TGGTATCAGCAGAAACCAGATGGAACTGTTAAACTCCTGATCTACCATACATC |
| AAGATTACACTCAGGAGTCCCATCAAGGTTCAGTGGCAGTGGGTCTGGAACA |
| GATTATTCTCTCACCATTAGCAACCTGGAGCAAGAAGATATTGCCACTTACTT |
| TTGCCAACAGGGTAATACGCTTCCGTACACGTTCGGAGGGGGGACCAAGCTG |
| GAGATCACAGGTGGCGGTGGCTCGGGCGGTGGTGGGTCGGGTGGCGGCGGA |
| TCTGAGGTGAAACTGCAGGAGTCAGGACCTGGCCTGGTGGCGCCCTCACAGA |
| GCCTGTCCGTCACATGCACTGTCTCAGGGGTCTCATTACCCGACTATGGTGTA |
| AGCTGGATTCGCCAGCCTCCACGAAAGGGTCTGGAGTGGCTGGGAGTAATAT |
| GGGGTAGTGAAACCACATACTATAATTCAGCTCTCAAATCCAGACTGACCATC |
| ATCAAGGACAACTCCAAGAGCCAAGTTTTCTTAAAAATGAACAGTCTGCAAAC |
| TGATGACACAGCCATTTACTACTGTGCCAAACATTATTACGGTGGTAGCT |
| ATGCTATGGACTACTGGGGCCAAGGAACCTCAGTCACCGTCTCCTCAGAGAG |
| CAAGTACGGCCCTCCCTGCCCCCCTTGCCCTGCCCCCGAGTTCCTGGGCGGACCCA |
| GCGTGTTCCTGTTCCCCCCCAAGCCCAAGGACACCCTGATGATCAGCCGGACCCCC |
| GAGGTGACCTGCGTGGTGGTGGACGTGAGCCAGGAAGATCCCGAGGTCCAGTTCA |
| ATTGGTACGTGGACGGCGTGGAAGTGCACAACGCCAAGACCAAGCCCAGAGAGG |
| AACAGTTCAACAGCACCTACCGGGTGGTGTCTGTGCTGACCGTGCTGCACCAGGA |
| CTGGCTGAACGGCAAAGAATACAAGTGCAAGGTGTCCAACAAGGGCCTGCCCAGC |
| AGCATCGAAAAGACCATCAGCAAGGCCAAGGGCCAGCCTCGCGAGCCCCAGGTGT |
| ACACCCTGCCTCCCTCCCAGGAAGAGATGACCAAGAACCAGGTGTCCCTGACCTG |
| CCTGGTGAAGGGCTTCTACCCCAGCGACATCGCCGTGGAGTGGGAGAGCAACGGC |
| CAGCCTGAGAACAACTACAAGACCACCCCTCCCGTGCTGGACAGCGACGGCAGCT |
| TCTTCCTGTACAGCCGGCTGACCGTGGACAAGAGCCGGTGGCAGGAAGGCAACGT |
| CTTTAGCTGCAGCGTGATGCACGAGGCCCTGCACAACCACTACACCCAGAAGAGC |
| CTGAGCCTGTCCCTGGGCAAG*ATGTTCTGGGTGCTGGTGGTGGTGGGCGGGGTGCTG* |
| *GCCTGCTACAGCCTGCTGGTGACAGTGGCCTTCATCATCTTTTGGGTGCGGAGCAAGCG* |
| *GAGCAGAGGCGGCCACAGCGACTACATGAACATGACCCCCAGACGGCCTGGCCCCAC* |
| *CCGGAAGCACTACCAGCCCTACGCCCCACCCAGGGACTTTGCCGCCTACCGGTCCGGC* |
| *GGAGGGCGGGTGAAGTTCAGCAGAAGCGCCGACGCCCCTGCCTACCAGCAGGGCC* |
| *AGAATCAGCTGTACAACGAGCTGAACCTGGGCAGAAGGGAAGAGTACGACGTCCT* |
| *GGATAAGCGGAGAGGCCGGGACCCTGAGATGGGCGGCAAGCCTCGGCGGAAGAA* |
| *CCCCCAGGAAGGCCTGTATAACGAACTGCAGAAAGACAAGATGGCCGAGGCCTAC* |
| *AGCGAGATCGGCATGAAGGGCGAGCGGAGGCGGGGCAAGGGCCACGACGGCCTG* |
| *TATCAGGGCCTGTCCACCGCCACCAAGGATACCTACGACGCCCTGCACATGCAGG* |
| *CCCTGCCCCCAAGG*CTCGAGGGCGGCGGAGAGGGCAGAGGAAGTCTTCTAACATG |
| CGGTGACGTGGAGGAGAATCCCGGCCCTCGCATGAGCGAGCTGATTAAGGAGAAC |
| ATGCACATGAAGCTGTACATGGAGGGCACCGTGGACAACCATCACTTCAAGTGCA |
| CATCCGAGGGCGAAGGCAAGCCCTACGAGGGCACCCAGACCATGAGAATCAAGG |
| TGGTCGAGGGCGGCCCTCTCCCCTTCGCCTTCGACATCCTGGCTACTAGCTTCCTCT |
| ACGGCAGCAAGACCTTCATCAACCACACCCAGGGCATCCCCGACTTCTTCAAGCA |
| GTCCTTCCCTGAGGGCTTCACATGGGAGAGAGTCACCACATACGAAGACGGGGGC |
| GTGCTGACCGCTACCCAGGACACCAGCCTCCAGGACGGCTGCCTCATCTACAACGT |
| CAAGATCAGAGGGGTGAACTTCACATCCAACGGCCCTGTGATGCAGAAGAAAACA |
| CTCGGCTGGGAGGCCTTCACCGAGACGCTGTACCCCGCTGACGGCGGCCTGGAAG |
| GCAGAAACGACATGGCCCTGAAGCTCGTGGGCGGGAGCCATCTGATCGCAAACAT |
| CAAGACCACATATAGATCCAAGAAACCCGCTAAGAACCTCAAGATGCCTGGCGTC |
| TACTATGTGGACTACAGACTGGAAAGAATCAAGGAGGCCAACAACGAAACATACG |
| TCGAGCAGCACGAGGTGGCAGTGGCCAGATACTGCGACCTCCCTAGCAAACTGGG |
| GCACAAGCTTAATTAA |

SEQUENCE LISTING

<160> NUMBER OF SEQ ID NOS: 24

<210> SEQ ID NO 1
<211> LENGTH: 122
<212> TYPE: PRT
<213> ORGANISM: Artificial Sequence
<220> FEATURE:
<223> OTHER INFORMATION: mSA2 affinity-enhanced streptavidin

<400> SEQUENCE: 1

Gly Ala Glu Ala Gly Ile Thr Gly Thr Trp Tyr Asn Gln His Gly Ser
1               5                   10                  15

Thr Phe Thr Val Thr Ala Gly Ala Asp Gly Asn Leu Thr Gly Gln Tyr
                20                  25                  30

Glu Asn Arg Ala Gln Gly Thr Gly Cys Gln Asn Ser Pro Tyr Thr Leu
            35                  40                  45

Thr Gly Arg Tyr Asn Gly Thr Lys Leu Glu Trp Arg Val Glu Trp Asn
        50                  55                  60

Asn Ser Thr Glu Asn Cys His Ser Arg Thr Glu Trp Arg Gly Gln Tyr
65                  70                  75                  80

Gln Gly Gly Ala Glu Ala Arg Ile Asn Thr Gln Trp Asn Leu Thr Tyr
                85                  90                  95

Glu Gly Gly Ser Gly Pro Ala Thr Glu Gln Gly Gln Asp Thr Phe Thr
            100                 105                 110

Lys Val Lys Pro Ser Ala Ala Ser Gly Ser
        115                 120

<210> SEQ ID NO 2
<211> LENGTH: 20
<212> TYPE: PRT
<213> ORGANISM: Mus musculus

<400> SEQUENCE: 2

Met Glu Thr Asp Thr Leu Leu Leu Trp Val Leu Leu Leu Trp Val Pro
1               5                   10                  15

Gly Ser Thr Gly
            20

<210> SEQ ID NO 3
<211> LENGTH: 22
<212> TYPE: PRT
<213> ORGANISM: Homo sapiens

<400> SEQUENCE: 3

Leu Leu Val Thr Ser Leu Leu Leu Cys Glu Leu Pro His Pro Ala Phe
1               5                   10                  15

Leu Leu Ile Pro Asp Thr
            20

<210> SEQ ID NO 4
<211> LENGTH: 17
<212> TYPE: PRT
<213> ORGANISM: Artificial Sequence
<220> FEATURE:
<223> OTHER INFORMATION: linker

<400> SEQUENCE: 4

Ser Ser Gly Gly Gly Gly Ser Gly Gly Gly Gly Ser Gly Gly Gly Gly
1               5                   10                  15

Ser

```
<210> SEQ ID NO 5
<211> LENGTH: 24
<212> TYPE: PRT
<213> ORGANISM: Homo sapiens

<400> SEQUENCE: 5

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 6
<211> LENGTH: 28
<212> TYPE: PRT
<213> ORGANISM: Homo sapiens

<400> SEQUENCE: 6

Met Phe Trp Val Leu Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 7
<211> LENGTH: 42
<212> TYPE: PRT
<213> ORGANISM: Homo sapiens

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 8
<211> LENGTH: 43
<212> TYPE: PRT
<213> ORGANISM: Homo sapiens

<400> SEQUENCE: 8

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Gly Gly Gly
            35                  40

<210> SEQ ID NO 9
<211> LENGTH: 110
<212> TYPE: PRT
<213> ORGANISM: Homo sapiens

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45
```

```
Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Gly Gly Gly
            100                 105                 110

<210> SEQ ID NO 10
<211> LENGTH: 112
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 11
<211> LENGTH: 626
<212> TYPE: PRT
<213> ORGANISM: Artificial Sequence
<220> FEATURE:
<223> OTHER INFORMATION: chimeric antigen receptor

<400> SEQUENCE: 11

Met Glu Thr Asp Thr Leu Leu Leu Trp Val Leu Leu Leu Trp Val Pro
1               5                   10                  15

Gly Ser Thr Gly Gly Ala Glu Ala Gly Ile Thr Gly Thr Trp Tyr Asn
            20                  25                  30

Gln His Gly Ser Thr Phe Thr Val Thr Ala Gly Ala Asp Gly Asn Leu
        35                  40                  45

Thr Gly Gln Tyr Glu Asn Arg Ala Gln Gly Thr Gly Cys Gln Asn Ser
    50                  55                  60

Pro Tyr Thr Leu Thr Gly Arg Tyr Asn Gly Thr Lys Leu Glu Trp Arg
65                  70                  75                  80

Val Glu Trp Asn Asn Ser Thr Glu Asn Cys His Ser Arg Thr Glu Trp
                85                  90                  95

Arg Gly Gln Tyr Gln Gly Gly Ala Glu Ala Arg Ile Asn Thr Gln Trp
            100                 105                 110

Asn Leu Thr Tyr Glu Gly Gly Ser Gly Pro Ala Thr Glu Gln Gly Gln
        115                 120                 125

Asp Thr Phe Thr Lys Val Lys Pro Ser Ala Ala Ser Gly Ser Thr Thr
    130                 135                 140

Thr Pro Ala Pro Arg Pro Pro Thr Pro Ala Pro Thr Ile Ala Ser Gln
```

```
                145                 150                 155                 160
        Pro Leu Ser Leu Arg Pro Glu Ala Cys Arg Pro Ala Ala Gly Gly Ala
                        165                 170                 175

Val His Thr Arg Gly Leu Asp Phe Ala Cys Asp Met Phe Trp Val Leu
                        180                 185                 190

Val Val Val Gly Gly Val Leu Ala Cys Tyr Ser Leu Leu Val Thr Val
                        195                 200                 205

Ala Phe Ile Ile Phe Trp Val Lys Arg Gly Arg Lys Lys Leu Leu Tyr
                    210                 215                 220

Ile Phe Lys Gln Pro Phe Met Arg Pro Val Gln Thr Thr Gln Glu Glu
        225                 230                 235                 240

Asp Gly Cys Ser Cys Arg Phe Pro Glu Glu Glu Glu Gly Gly Cys Glu
                        245                 250                 255

Leu Arg Val Lys Phe Ser Arg Ser Ala Asp Ala Pro Ala Tyr Gln Gln
                        260                 265                 270

Gly Gln Asn Gln Leu Tyr Asn Glu Leu Asn Leu Gly Arg Arg Glu Glu
                    275                 280                 285

Tyr Asp Val Leu Asp Lys Arg Arg Gly Arg Asp Pro Glu Met Gly Gly
                    290                 295                 300

Lys Pro Arg Arg Lys Asn Pro Gln Glu Gly Leu Tyr Asn Glu Leu Gln
        305                 310                 315                 320

Lys Asp Lys Met Ala Glu Ala Tyr Ser Glu Ile Gly Met Lys Gly Glu
                        325                 330                 335

Arg Arg Arg Gly Lys Gly His Asp Gly Leu Tyr Gln Gly Leu Ser Thr
                        340                 345                 350

Ala Thr Lys Asp Thr Tyr Asp Ala Leu His Met Gln Ala Leu Pro Pro
                    355                 360                 365

Arg Leu Glu Gly Gly Gly Glu Gly Arg Gly Ser Leu Leu Thr Cys Gly
                    370                 375                 380

Asp Val Glu Glu Asn Pro Gly Pro Arg Met Ser Glu Leu Ile Lys Glu
        385                 390                 395                 400

Asn Met His Met Lys Leu Tyr Met Glu Gly Thr Val Asp Asn His His
                        405                 410                 415

Phe Lys Cys Thr Ser Glu Gly Glu Gly Lys Pro Tyr Glu Gly Thr Gln
                        420                 425                 430

Thr Met Arg Ile Lys Val Val Glu Gly Gly Pro Leu Pro Phe Ala Phe
                    435                 440                 445

Asp Ile Leu Ala Thr Ser Phe Leu Tyr Gly Ser Lys Thr Phe Ile Asn
        450                 455                 460

His Thr Gln Gly Ile Pro Asp Phe Phe Lys Gln Ser Phe Pro Glu Gly
        465                 470                 475                 480

Phe Thr Trp Glu Arg Val Thr Thr Tyr Glu Asp Gly Gly Val Leu Thr
                        485                 490                 495

Ala Thr Gln Asp Thr Ser Leu Gln Asp Gly Cys Leu Ile Tyr Asn Val
                        500                 505                 510

Lys Ile Arg Gly Val Asn Phe Thr Ser Asn Gly Pro Val Met Gln Lys
                    515                 520                 525

Lys Thr Leu Gly Trp Glu Ala Phe Thr Glu Thr Leu Tyr Pro Ala Asp
                    530                 535                 540

Gly Gly Leu Glu Gly Arg Asn Asp Met Ala Leu Lys Leu Val Gly Gly
        545                 550                 555                 560

Ser His Leu Ile Ala Asn Ile Lys Thr Thr Tyr Arg Ser Lys Lys Pro
                        565                 570                 575
```

Ala Lys Asn Leu Lys Met Pro Gly Val Tyr Tyr Val Asp Tyr Arg Leu
            580                 585                 590

Glu Arg Ile Lys Glu Ala Asn Asn Glu Thr Tyr Val Glu Gln His Glu
        595                 600                 605

Val Ala Val Ala Arg Tyr Cys Asp Leu Pro Ser Lys Leu Gly His Lys
    610                 615                 620

Leu Asn
625

<210> SEQ ID NO 12
<211> LENGTH: 628
<212> TYPE: PRT
<213> ORGANISM: Artificial Sequence
<220> FEATURE:
<223> OTHER INFORMATION: chimeric antigen receptor

<400> SEQUENCE: 12

Met Glu Thr Asp Thr Leu Leu Leu Trp Val Leu Leu Leu Trp Val Pro
1               5                   10                  15

Gly Ser Thr Gly Gly Ala Glu Ala Gly Ile Thr Gly Thr Trp Tyr Asn
            20                  25                  30

Gln His Gly Ser Thr Phe Thr Val Thr Ala Gly Ala Asp Gly Asn Leu
        35                  40                  45

Thr Gly Gln Tyr Glu Asn Arg Ala Gln Gly Thr Gly Cys Gln Asn Ser
    50                  55                  60

Pro Tyr Thr Leu Thr Gly Arg Tyr Asn Gly Thr Lys Leu Glu Trp Arg
65                  70                  75                  80

Val Glu Trp Asn Asn Ser Thr Glu Asn Cys His Ser Arg Thr Glu Trp
                85                  90                  95

Arg Gly Gln Tyr Gln Gly Gly Ala Glu Ala Arg Ile Asn Thr Gln Trp
            100                 105                 110

Asn Leu Thr Tyr Glu Gly Gly Ser Gly Pro Ala Thr Glu Gln Gly Gln
        115                 120                 125

Asp Thr Phe Thr Lys Val Lys Pro Ser Ala Ala Ser Gly Ser Thr Thr
    130                 135                 140

Thr Pro Ala Pro Arg Pro Pro Thr Pro Ala Pro Thr Ile Ala Ser Gln
145                 150                 155                 160

Pro Leu Ser Leu Arg Pro Glu Ala Cys Arg Pro Ala Ala Gly Gly Ala
                165                 170                 175

Val His Thr Arg Gly Leu Asp Phe Ala Cys Asp Met Phe Trp Val Leu
            180                 185                 190

Val Val Val Gly Gly Val Leu Ala Cys Tyr Ser Leu Leu Val Thr Val
        195                 200                 205

Ala Phe Ile Ile Phe Trp Val Arg Ser Lys Arg Ser Arg Gly Gly His
    210                 215                 220

Ser Asp Tyr Met Asn Met Thr Pro Arg Arg Pro Gly Pro Thr Arg Lys
225                 230                 235                 240

His Tyr Gln Pro Tyr Ala Pro Pro Arg Asp Phe Ala Ala Tyr Arg Ser
                245                 250                 255

Gly Gly Gly Arg Val Lys Phe Ser Arg Ser Ala Asp Ala Pro Ala Tyr
            260                 265                 270

Gln Gln Gly Gln Asn Gln Leu Tyr Asn Glu Leu Asn Leu Gly Arg Arg
        275                 280                 285

Glu Glu Tyr Asp Val Leu Asp Lys Arg Arg Gly Arg Asp Pro Glu Met
    290                 295                 300

-continued

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
                325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
        355                 360                 365

Pro Pro Arg Leu Glu Gly Gly Glu Gly Arg Gly Ser Leu Leu Thr
370                 375                 380

Cys Gly Asp Val Glu Glu Asn Pro Gly Pro Arg Met Ser Glu Leu Ile
385                 390                 395                 400

Lys Glu Asn Met His Met Lys Leu Tyr Met Glu Gly Thr Val Asp Asn
                405                 410                 415

His His Phe Lys Cys Thr Ser Glu Gly Glu Gly Lys Pro Tyr Glu Gly
            420                 425                 430

Thr Gln Thr Met Arg Ile Lys Val Val Glu Gly Gly Pro Leu Pro Phe
        435                 440                 445

Ala Phe Asp Ile Leu Ala Thr Ser Phe Leu Tyr Gly Ser Lys Thr Phe
450                 455                 460

Ile Asn His Thr Gln Gly Ile Pro Asp Phe Phe Lys Gln Ser Phe Pro
465                 470                 475                 480

Glu Gly Phe Thr Trp Glu Arg Val Thr Thr Tyr Glu Asp Gly Gly Val
                485                 490                 495

Leu Thr Ala Thr Gln Asp Thr Ser Leu Gln Asp Gly Cys Leu Ile Tyr
            500                 505                 510

Asn Val Lys Ile Arg Gly Val Asn Phe Thr Ser Asn Gly Pro Val Met
        515                 520                 525

Gln Lys Lys Thr Leu Gly Trp Glu Ala Phe Thr Glu Thr Leu Tyr Pro
530                 535                 540

Ala Asp Gly Gly Leu Glu Gly Arg Asn Asp Met Ala Leu Lys Leu Val
545                 550                 555                 560

Gly Gly Ser His Leu Ile Ala Asn Ile Lys Thr Thr Tyr Arg Ser Lys
                565                 570                 575

Lys Pro Ala Lys Asn Leu Lys Met Pro Gly Val Tyr Tyr Val Asp Tyr
            580                 585                 590

Arg Leu Glu Arg Ile Lys Glu Ala Asn Asn Glu Thr Tyr Val Glu Gln
        595                 600                 605

His Glu Val Ala Val Ala Arg Tyr Cys Asp Leu Pro Ser Lys Leu Gly
610                 615                 620

His Lys Leu Asn
625

<210> SEQ ID NO 13
<211> LENGTH: 60
<212> TYPE: DNA
<213> ORGANISM: Mus musculus

<400> SEQUENCE: 13
atggagacag acacactcct gctatgggtg ctgctgctct gggttccagg ttccacaggt    60

<210> SEQ ID NO 14
<211> LENGTH: 364
<212> TYPE: DNA
<213> ORGANISM: Artificial Sequence

```
<220> FEATURE:
<223> OTHER INFORMATION: nucleic acid encoding high affinity
      streptavidin

<400> SEQUENCE: 14
gcgcagaggc gggtatcacc gggacatggt acaaccaaca cggaagcaca tttacagtca      60
ccgctggagc agacgggaat ctgaccggac agtacgagaa cagggctcag gggacaggtt     120
gtcagaacag tccgtatact ctgactggga ggtacaatgg cacgaagctg agtggcgag      180 tcgagtggaa taattccacg gaaaactgtc acagtagaac agagtggagg ggacagtacc     240 agggggagc agaggcccgg atcaacaccc aatggaactt gacatatgaa ggcgggtcag      300
gccccgcgac agagcaagga caggatacat tcacgaaggt caagccaagc gcagcctctg     360
gctc                                                                  364

<210> SEQ ID NO 15
<211> LENGTH: 135
<212> TYPE: DNA
<213> ORGANISM: Homo sapiens

<400> SEQUENCE: 15
accacaactc cagctccccg gccccctact cctgctccaa ccattgcctc acagccactg      60
agcctgcggc ccgaagcttg tagacctgct gctggaggag ctgtgcatac cagaggcctg     120
gacttcgcct gcgat                                                      135

<210> SEQ ID NO 16
<211> LENGTH: 84
<212> TYPE: DNA
<213> ORGANISM: Homo sapiens

<400> SEQUENCE: 16
atgttctggg tgctggtggt ggtgggcggg gtgctggcct gctacagcct gctggtgaca      60
gtggccttca tcatcttttg ggtg                                            84

<210> SEQ ID NO 17
<211> LENGTH: 126
<212> TYPE: DNA
<213> ORGANISM: Homo sapiens

<400> SEQUENCE: 17
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 18
<211> LENGTH: 132
<212> TYPE: DNA
<213> ORGANISM: Homo sapiens

<400> SEQUENCE: 18
cggagcaagc ggagcagagg cggccacagc gactacatga acatgacccc cagacggcct      60
ggccccaccc ggaagcacta ccagccctac gccccaccca gggactttgc cgcctaccgg     120
tccggcggag gg                                                         132

<210> SEQ ID NO 19
<211> LENGTH: 336
<212> TYPE: DNA
<213> ORGANISM: Homo sapiens
```

<400> SEQUENCE: 19

```
cgggtgaagt tcagcagaag cgccgacgcc cctgcctacc agcagggcca gaatcagctg      60
tacaacgagc tgaacctggg cagaagggaa gagtacgacg tcctggataa gcggagaggc     120
cgggaccctg agatgggcgg caagcctcgg cggaagaacc cccaggaagg cctgtataac     180
gaactgcaga agacaagat ggccgaggcc tacagcgaga tcggcatgaa gggcgagcgg      240
aggcggggca agggccacga cggcctgtat cagggcctgt ccaccgccac caaggatacc     300
tacgacgccc tgcacatgca ggccctgccc ccaagg                               336
```

<210> SEQ ID NO 20
<211> LENGTH: 1113
<212> TYPE: DNA
<213> ORGANISM: Artificial Sequence
<220> FEATURE:
<223> OTHER INFORMATION: nucleic acid sequence encoding a chimeric
      antigen receptor

<400> SEQUENCE: 20

```
atggagacag acacactcct gctatgggtg ctgctgctct ggttccagg ttccacaggt       60
ggcgcagagg cgggtatcac cgggacatgg tacaaccaac acggaagcac atttacagtc    120
accgctggag cagacgggaa tctgaccgga cagtacgaga cagggctca ggggacaggt     180
tgtcagaaca gtccgtatac tctgactggg aggtacaatg cacgaagct ggagtggcga     240
gtcgagtgga ataattccac ggaaaactgt cacagtagaa cagagtggag gggacagtac    300
caggggggag cagaggcccg gatcaacacc aatggaact tgacatatga aggcgggtca     360
ggccccgcga cagagcaagg acaggataca ttcacgaagg tcaagccaag cgcagcctct    420
ggctctacca caactccagc tccccggccc cctactcctg ctccaaccat tgcctcacag    480
ccactgagcc tgcggcccga agcttgtaga cctgctgctg gaggagctgt gcataccaga    540
ggcctggact cgcctgcga tatgttctgg gtgctggtgg tggtgggcgg ggtgctggcc     600
tgctacagcc tgctggtgac agtggccttc atcatctttt gggtgcggag caagcggagc    660
agaggcggcc acagcgacta catgaacatg accccagac ggcctggccc cacccggaag     720
cactaccagc cctacgcccc acccagggac tttgccgcct accgtccgg cggagggcgg     780
gtgaagttca gcagaagcgc cgacgcccct gcctaccagc agggccagaa tcagctgtac    840
aacgagctga acctgggcag aagggaagag tacgacgtcc tggataagcg agaggccgg     900
gaccctgaga tgggcggcaa gcctcggcgg aagaaccccc aggaaggcct gtataacgaa    960
ctgcagaaag acaagatggc cgaggcctac agcgagatcg gcatgaaggg cgagcggagg   1020
cggggcaagg gccacgacgg cctgtatcag ggcctgtcca ccgccaccaa ggataccctac  1080
gacgccctgc acatgcaggc cctgccccca agg                                1113
```

<210> SEQ ID NO 21
<211> LENGTH: 1107
<212> TYPE: DNA
<213> ORGANISM: Artificial Sequence
<220> FEATURE:
<223> OTHER INFORMATION: nucleic acid encoding a chimeric antigen
      receptor

<400> SEQUENCE: 21

```
atggagacag acacactcct gctatgggtg ctgctgctct ggttccagg ttccacaggt       60
ggcgcagagg cgggtatcac cgggacatgg tacaaccaac acggaagcac atttacagtc    120
```

```
accgctggag cagacgggaa tctgaccgga cagtacgaga cagggctca ggggacaggt      180 tgtcagaaca gtccgtatac tctgactggg aggtacaatg cacgaagct ggagtggcga      240 gtcgagtgga ataattccac ggaaaactgt cacagtagaa cagagtggag gggacagtac      300
caggggggag cagaggcccg gatcaacacc caatggaact tgacatatga aggcgggtca      360
ggccccgcga cagagcaagg acaggataca ttcacgaagg tcaagccaag cgcagcctct      420
ggctctacca caactccagc tccccggccc cctactcctg ctccaaccat tgcctcacag      480
ccactgagcc tgcggcccga agcttgtaga cctgctgctg gaggagctgt gcataccaga      540
ggcctggact cgcctgcga tatgttctgg gtgctggtgg tggtgggcgg ggtgctggcc       600
tgctacagcc tgctggtgac agtggccttc atcatctttt gggtgaaacg gggcagaaag      660
aaactcctgt atatattcaa caaccatttt atgagaccag tacaaactac tcaagaggaa      720
gatggctgta gctgccgatt ccagaagaa gaagaaggag gatgtgaact gcgggtgaag      780
ttcagcagaa gcgccgacgc ccctgcctac cagcagggcc agaatcagct gtacaacgag      840
ctgaacctgg gcagaaggga gagtacgac gtcctggata gcggagagg ccgggaccct       900 gagatgggcg gcaagcctcg gcggaagaac ccccaggaag gcctgtataa cgaactgcag      960
aaagacaaga tggccgaggc ctacagcgag atcggcatga agggcgagcg gaggcggggc     1020
aagggccacg acggcctgta tcagggcctg tccaccgcca ccaaggatac ctacgacgcc     1080
ctgcacatgc aggccctgcc cccaagg                                         1107
```

<210> SEQ ID NO 22
<211> LENGTH: 1887
<212> TYPE: DNA
<213> ORGANISM: Artificial Sequence
<220> FEATURE:
<223> OTHER INFORMATION: nucleic acid encoding a chimeric antigen receptor

<400> SEQUENCE: 22

```
atggagacag acacactcct gctatgggtg ctgctgctct gggttccagg ttccacaggt       60
ggcgcagagg cgggtatcac cgggacatgg tacaaccaac acggaagcac atttacagtc      120
accgctggag cagacgggaa tctgaccgga cagtacgaga cagggctca ggggacaggt      180 tgtcagaaca gtccgtatac tctgactggg aggtacaatg cacgaagct ggagtggcga      240 gtcgagtgga ataattccac ggaaaactgt cacagtagaa cagagtggag gggacagtac      300
caggggggag cagaggcccg gatcaacacc caatggaact tgacatatga aggcgggtca      360
ggccccgcga cagagcaagg acaggataca ttcacgaagg tcaagccaag cgcagcctct      420
ggctctacca caactccagc tccccggccc cctactcctg ctccaaccat tgcctcacag      480
ccactgagcc tgcggcccga agcttgtaga cctgctgctg gaggagctgt gcataccaga      540
ggcctggact cgcctgcga tatgttctgg gtgctggtgg tggtgggcgg ggtgctggcc       600
tgctacagcc tgctggtgac agtggccttc atcatctttt gggtgcgag caagcggagc      660 agaggcggcc acagcgacta catgaacatg ccccccagac ggcctggccc cacccggaag      720
cactaccagc cctacgcccc acccaggac tttgccgcct accggtccgg cggagggcgg      780
gtgaagttca gcagaagcgc cgacgcccct gcctaccaga gggcagaa tcagctgtac      840 aacgagctga acctgggcag aagggaagag tacgacgtcc tggataagcg gagaggccgg      900
gaccctgaga tgggcggcaa gcctcggcgg aagaacccccc aggaaggcct gtataacgaa      960
ctgcagaaag acaagatggc cgaggcctac agcgagatcg gcatgaaggg cgagcggagg     1020
```

| | |
|---|---|
| cggggcaagg gccacgacgg cctgtatcag ggcctgtcca ccgccaccaa ggatacctac | 1080 |
| gacgccctgc acatgcaggc cctgcccca aggctcgagg gcggcggaga gggcagagga | 1140 |
| agtcttctaa catgcggtga cgtggaggag aatcccggcc ctcgcatgag cgagctgatt | 1200 |
| aaggagaaca tgcacatgaa gctgtacatg gagggcaccg tggacaacca tcacttcaag | 1260 |
| tgcacatccg agggcgaagg caagccctac gagggcaccc agaccatgag aatcaaggtg | 1320 |
| gtcgagggcg ccctctccc cttcgccttc gacatcctgg ctactagctt cctctacggc | 1380 |
| agcaagacct tcatcaacca cacccagggc atccccgact tcttcaagca gtccttccct | 1440 |
| gagggcttca catgggagag agtcaccaca tacgaagacg gggcgtgct gaccgctacc | 1500 |
| caggacacca gcctccagga cggctgcctc atctacaacg tcaagatcag aggggtgaac | 1560 |
| ttcacatcca acggcctgt gatgcagaag aaaacactcg gctgggaggc cttcaccgag | 1620 |
| acgctgtacc ccgctgacgg cggcctggaa ggcagaaacg acatggccct gaagctcgtg | 1680 |
| ggcgggagcc atctgatcgc aaacatcaag accacatata gatccaagaa acccgctaag | 1740 |
| aacctcaaga tgcctggcgt ctactatgtg gactacagac tggaaagaat caaggaggcc | 1800 |
| aacaacgaaa catacgtcga gcagcacgag gtggcagtgg ccagatactg cgacctccct | 1860 |
| agcaaactgg ggcacaagct taattaa | 1887 |

<210> SEQ ID NO 23
<211> LENGTH: 1881
<212> TYPE: DNA
<213> ORGANISM: Artificial Sequence
<220> FEATURE:
<223> OTHER INFORMATION: nucleic acid encodng a chimeric antigen
      receptor

<400> SEQUENCE: 23

| | |
|---|---|
| atggagacag acacactcct gctatgggtg ctgctgctct ggttccagg ttccacaggt | 60 |
| ggcgcagagg cgggtatcac cggacatgg tacaaccaac acggaagcac atttacagtc | 120 |
| accgctggag cagacgggaa tctgaccgga cagtacgaga cagggctca ggggacaggt | 180 |
| tgtcagaaca gtccgtatac tctgactggg aggtacaatg gcacgaagct ggagtggcga | 240 |
| gtcgagtgga ataattccac ggaaaactgt cacagtagaa cagagtggag gggacagtac | 300 |
| cagggggag cagaggcccg gatcaacacc caatggaact tgacatatga aggcgggtca | 360 |
| ggccccgcga cagagcaagg acaggataca ttcacgaagg tcaagccaag cgcagcctct | 420 |
| ggctctacca caactccagc tccccggccc ctactcctg ctccaaccat gcctcacag | 480 |
| ccactgagcc tgcggcccga agcttgtaga cctgctgctg gaggagctgt gcataccaga | 540 |
| ggcctggact cgcctgcga tatgttctgg gtgctggtgg tggtgggcgg ggtgctggcc | 600 |
| tgctacagcc tgctggtgac agtggccttc atcatctttt gggtgaaacg gggcagaaag | 660 |
| aaactcctgt atatattcaa acaaccattt atgagaccag tacaaactac tcaagaggaa | 720 |
| gatggctgta gctgccgatt ccagaagaa aagaaggag atgtgaact gcgggtgaag | 780 |
| ttcagcagaa gcgccgacgc ccctgcctac cagcagggcc agaatcagct gtacaacgag | 840 |
| ctgaacctgg gcagaaggga agagtacgac gtcctggata gcggagagg ccggacccct | 900 |
| gagatgggcg gcaagcctcg gcggaagaac ccccaggaag cctgtataa cgaactgcag | 960 |
| aaagacaaga tggccgaggc ctacagcgag atcggcatga agggcgagcg gaggcgggc | 1020 |
| aagggccacg acgcctgta tcagggcctg tccaccgcca ccaaggatac ctacgacgcc | 1080 |
| ctgcacatgc aggccctgcc cccaaggctc gagggcggcg gagagggcag aggaagtctt | 1140 |

-continued

```
ctaacatgcg gtgacgtgga ggagaatccc ggccctcgca tgagcgagct gattaaggag      1200
aacatgcaca tgaagctgta catggagggc accgtggaca accatcactt caagtgcaca      1260
tccgagggcg aaggcaagcc ctacgagggc acccagacca tgagaatcaa ggtggtcgag      1320
ggcggccctc tccccttcgc cttcgacatc ctggctacta gcttcctcta cggcagcaag      1380
accttcatca accacaccca gggcatcccc gacttcttca gcagtccttc cctgagggc       1440 ttcacatggg agagagtcac cacatacgaa gacgggggcg tgctgaccgc tacccaggac      1500
accagcctcc aggacggctg cctcatctac aacgtcaaga tcagaggggt gaacttcaca      1560
tccaacggcc ctgtgatgca gaagaaaaca ctcggctggg aggccttcac cgagacgctg      1620
taccccgctg acggcggcct ggaaggcaga aacgacatgg ccctgaagct cgtgggcggg      1680
agccatctga tcgcaaacat caagaccaca tatagatcca agaaacccgc taagaacctc      1740
aagatgcctg gcgtctacta tgtggactac agactggaaa gaatcaagga ggccaacaac      1800
gaaacatacg tcgagcagca cgaggtggca gtggccagat actgcgacct ccctagcaaa      1860
ctggggcaca agcttaatta a                                                1881
```

```
<210> SEQ ID NO 24
<211> LENGTH: 2799
<212> TYPE: DNA
<213> ORGANISM: Artificial Sequence
<220> FEATURE:
<223> OTHER INFORMATION: nucleic acid encoding a chimeric antigen
      receptor

<400> SEQUENCE: 24
```

```
atggagacag acacactcct gctatgggtg ctgctgctct gggttccagg ttccacaggt        60
gacatccaga tgacacagac tacatcctcc ctgtctgcct ctctgggaga cagagtcacc       120
atcagttgca gggcaagtca ggacattagt aaatatttaa attggtatca gcagaaacca       180
gatggaactg ttaaactcct gatctaccat acatcaagat acactcagg agtcccatca        240 aggttcagtg gcagtgggtc tggaacagat tattctctca ccattagcaa cctggagcaa       300
gaagatattg ccacttactt ttgccaacag ggtaatacgc ttccgtacac gttcggaggg       360
gggaccaagc tggagatcac aggtggcggt ggctcgggcg tggtgggtc gggtggcggc        420 ggatctgagg tgaaactgca ggagtcagga cctggcctgg tggcgccctc acagagcctg       480
tccgtcacat gcactgtctc aggggtctca ttacccgact atggtgtaag ctggattcgc       540
cagcctccac gaaagggtct ggagtggctg ggagtaatat ggggtagtga aaccacatac       600
tataattcag ctctcaaatc cagactgacc atcatcaagg acaactccaa gagccaagtt       660
ttcttaaaaa tgaacagtct gcaaactgat gacacagcca tttactactg tgccaaacat       720
tattactacg gtggtagcta tgctatggac tactggggcc aaggaacctc agtcaccgtc       780
tcctcagaga gcaagtacgg ccctcctgc ccccttgcc ctgccccga gttcctgggc          840 ggacccagcg tgttcctgtt ccccccaag cccaaggaca ccctgatgat cagccggacc        900
cccgaggtga cctgcgtggt ggtggacgtg agccaggaag atcccgaggt ccagttcaat       960
tggtacgtgg acggcgtgga agtgcacaac gccaagacca gcccagaga ggaacagttc      1020 aacagcacct accgggtggt gtctgtgctg accgtgctgc accaggactg gctgaacggc      1080
aaagaataca agtgcaaggt gtccaacaag ggcctgccca gcagcatcga aaagaccatc      1140
agcaaggcca gggccagcc tcgcgagccc caggtgtaca ccctgcctcc ctcccaggaa       1200
gagatgacca agaaccaggt gtccctgacc tgcctggtga agggcttcta ccccagcgac      1260
```

```
atcgccgtgg agtgggagag caacggccag cctgagaaca actacaagac cacccctccc    1320
gtgctggaca gcgacggcag cttcttcctg tacagccggc tgaccgtgga caagagccgg    1380
tggcaggaag gcaacgtctt tagctgcagc gtgatgcacg aggccctgca caaccactac    1440
acccagaaga gcctgagcct gtccctgggc aagatgttct gggtgctggt ggtggtgggc    1500
ggggtgctgg cctgctacag cctgctggtg acagtggcct tcatcatctt ttgggtgcgg    1560
agcaagcgga gcagaggcgg ccacagcgac tacatgaaca tgaccccccag acggcctggc    1620 cccacccgga agcactacca gccctacgcc ccacccaggg actttgccgc ctaccggtcc    1680
ggcggagggc gggtgaagtt cagcagaagc gccgacgccc ctgcctacca gcagggccag    1740
aatcagctgt acaacgagct gaacctgggc agaagggaag agtacgacgt cctggataag    1800
cggagaggcc gggaccctga gatgggcggc aagcctcggc ggaagaaccc ccaggaaggc    1860
ctgtataacg aactgcagaa agacaagatg gccgaggcct acagcgagat cggcatgaag    1920
ggcgagcgga ggcggggcaa gggccacgac ggcctgtatc agggcctgtc caccgccacc    1980
aaggatacct acgacgccct gcacatgcag gccctgcccc caaggctcga gggcggcgga    2040
gagggcagag gaagtcttct aacatgcggt gacgtggagg agaatcccgg ccctcgcatg    2100
agcgagctga ttaaggagaa catgcacatg aagctgtaca tggagggcac cgtggacaac    2160
catcacttca gtgcacatc cgagggcgaa ggcaagccct acgagggcac ccagaccatg    2220
agaatcaagg tggtcgaggg cggccctctc cccttcgcct tcgacatcct ggctactagc    2280
ttcctctacg gcagcaagac cttcatcaac cacacccagg gcatccccga cttcttcaag    2340
cagtccttcc ctgagggctt cacatgggag agagtcacca catacgaaga cggggggcgtg    2400 ctgaccgcta cccaggacac cagcctccag gacggctgcc tcatctacaa cgtcaagatc    2460
agaggggtga acttcacatc caacggccct gtgatgcaga agaaaacact cggctgggag    2520
gccttcaccg agacgctgta ccccgctgac ggcggcctgg aaggcagaaa cgacatggcc    2580
ctgaagctcg tgggcgggag ccatctgatc gcaaacatca agaccacata tagatccaag    2640
aaacccgcta agaacctcaa gatgcctggc gtctactatg tggactacag actggaaaga    2700
atcaaggagg ccaacaacga aacatacgtc gagcagcacg aggtggcagt ggccagatac    2760
tgcgacctcc ctagcaaact ggggcacaag cttaattaa                            2799
```

AFFINITY-ENHANCED MONOMERIC STREPTAVIDIN CHIMERIC ANTIGEN RECEPTOR (CAR)

CROSS REFERENCE TO RELATED APPLICATION(S)

This claims the benefit of U.S. Provisional Application No. 62/584,601, filed Nov. 10, 2017, which is incorporated herein by reference in its entirety.

ACKNOWLEDGMENT OF GOVERNMENT SUPPORT

This invention was made with government support under CA210039 awarded by the National Institutes of Health. The government has certain rights in the invention.

FIELD

This relates to the field of immunotherapeutics, specifically to chimeric antigen receptor T cells.

BACKGROUND

Chimeric antigen receptors (CARs) are synthetic T cell receptors used to re-direct T cell effector functions toward tumor associated antigens (TAAs) (Maude et al., The New Engl. J. Med. 2014; 371:1507-17; Gross et al., Proc Natl Acad Sci U S A 1989; 86:10024-8). Commonly consisting of a TAA-specific antibody single chain variable fragment (scFv) fused via a spacer and transmembrane domain to intracellular T cell signaling domains, when a CAR binds to its target antigen, T cell signaling is initiated leading to target cell lysis, cytokine production and cell proliferation (Sadelain et al., Cancer discovery 2013; 3:388-98). Clinical trials with adoptively transferred CAR T cells targeting the B cell antigen CD19 have been highly successful in treating refractory acute lymphoblastic leukemia, and there is much interest in expanding the antigens targeted by CARs and the number of cancers that can be treated (Maude et al., The New Engl. J. Med. 2014; 371:1507-17; Grupp et al., The New Engl. J. Med. 2013; 368:1509-18; Park et al., Blood 2014; 124:382; Porter et al., The New Engl. J. Med. 2011; 365:725-33; Lohmueller and Finn, Pharmacol Ther 2017). Despite this success and interest, many challenges remain to expanding the application of CAR therapy. The single antigen specificity of CARs can render them ineffective against tumors that lack expression of the target antigen due to antigen loss or tumor heterogeneity (Ruella et al., J Clin Invest 2016; 126:3814-260. Additionally, the unregulated persistence of CAR activity can cause cytokine release syndrome and other toxicities (Lee et al., Blood 2014; 124:188-95). For targeting new cancers, the creation of new CARs is needed, which is technically challenging and requires extensive engineering and safety testing to rule out off-tumor toxicities (Khalil et al., Nat Rev Clin Oncol 2016; 13:394).

SUMMARY

An approach that addresses the challenges of CAR T cells is the creation of CARs that bind to common tag molecules—such as fluorescein isothiocyanate (FITC), peptide neo-epitopes (PNE), Fcγ, and biotin—that are conjugated to TAA-specific antibodies (Rodgers et al., Proc Natl Acad Sci U S A 2016; 113:E459-68; Tamada et al., Clin Cancer Res 2012; 18:6436-45; Urbanska et al., Cancer Res 2012; 72:1844-52; Kudo et al., Cancer Res 2014; 74:93-103). This "anti-tag CAR" (AT-CAR) therapy is designed so that patients are infused with a tagged, TAA-specific antibody that binds to tumor cells, followed by T cells expressing AT-CARs that react with the tagged antibodies on tumor cells (FIG. 1A). This approach allows for sequential or simultaneous targeting of multiple tumor antigens with different antibodies (Urbanska and Powell, Oncoimmunology 2012; 1:777-9). In some embodiments, the activity of AT-CARs can be regulated by altering the concentration of tagged antibodies or halting antibody administration for better control over potential toxicities (Ma et al., Proc Natl Acad Sci U S A 2016; 113:E450-8).

An AT-CAR was developed with potent activity composed of the affinity-enhanced monomeric streptavidin (mSA2) protein, engineered to have high affinity for biotin compared to other monomeric and dimeric avidins. In some embodiments, a chimeric antigen receptor is disclosed that includes: (a) an extracellular high affinity streptavidin b) a hinge domain from CD8; (c) a CD28 transmembrane domain; (d) a signaling domain, such as, but not limited to, an intracellular 4-1BB or D28 signaling domain; and (e) an intracellular CD3 zeta signaling domain, wherein (a)-(e) are in N-terminal to C-terminal order. In additional embodiments, nucleic acids encoding this chimeric antigen receptor, vectors including these nucleic acids, and T and natural killer (NK) cells transformed with this chimeric antigen receptor are also disclosed. In further embodiments, pharmaceutical compositions are disclosed that include these nucleic acids, and T and natural killer (NK) cells transformed with this chimeric antigen receptor.

In further embodiments, methods are disclosed for treating a subject with a tumor. The methods include administering to the subject a therapeutically effective amount of an antibody or aptamer that specifically binds a tumor associated antigen expressed by the tumor, wherein the antibody or aptamer is biotinylated, and administering to the subject the pharmaceutical composition including a nucleic acids encoding the CAR, and/or T and natural killer (NK) cells transformed with this chimeric antigen receptor.

The foregoing and other objects, features, and advantages of the invention will become more apparent from the following detailed description, which proceeds with reference to the accompanying figures.

BRIEF DESCRIPTION OF THE DRAWINGS

FIGS. 7A-7C provides the nucleic acid sequences (SEQ ID NOs: 22-24) encoding the CARs used in the studies disclosed herein. SEQ ID NO: 22 is a nucleic acid sequence encoding a mSA2-CD28ζ CAR. SEQ ID NO: 23 is a nucleic acid sequence encoding a mSA2-41BBζ CAR. SEQ ID NO: 24 is a nucleic acid sequence encoding a CAR that was used as a control in the experimental studies. The sequences are all codon optimized for expression in humans. Legend:
Leader sequence: Underline
mSA2: bold
CD8αhinge: Double Underline
CD28-TM,cyto: Italics
CD3zeta: Dashed underline
T2A-TagBFP: Plain text (no demarcation)
4-1BB: Arial font and jagged underline
FMC63: bold and double jagged underline
IgG4(hinge,CH2,CH3): Dotted underline

SEQUENCE LISTING

Figures 1A, 1B:
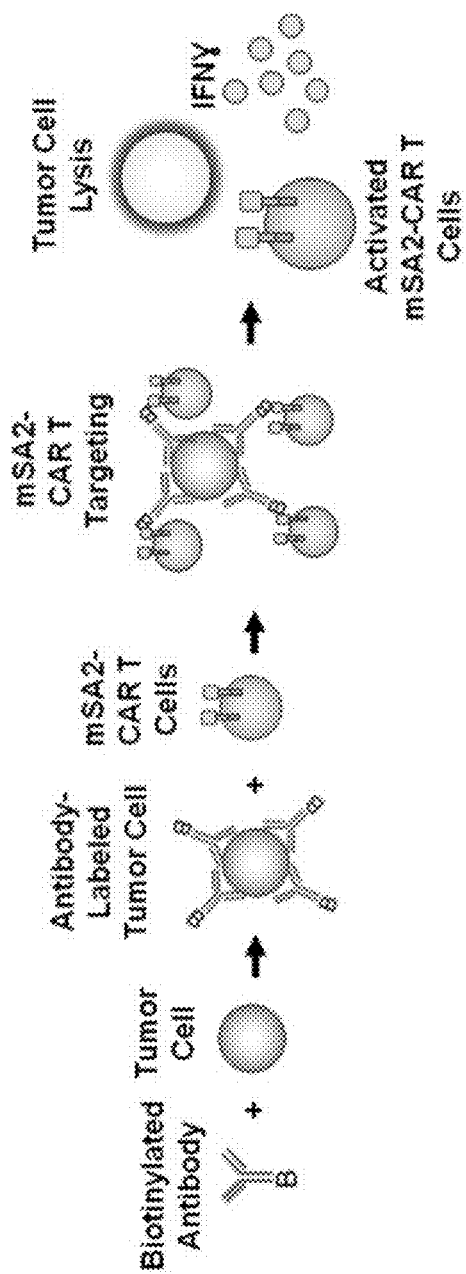
FIGS. 1A-1B. Schematic of the function and vector design of mSA2 anti-biotin CARs. (A) A tumor-specific antibody that is biotinylated encounters and binds to its target antigen on a tumor cell while simultaneously providing biotin as a new target. Avidin-bearing mSA2 CAR T cells recognize the biotin as their specific target, which leads to their activation, cytokine production and tumor cell lysis. (B) Designs of the mSA2-41BBζ and mSA2-CD28ζ CAR lentiviral expression constructs and the positive control FMC63-CD28ζ anti-CD19 CAR construct.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-99689-02_Sequence-_Listing.txt, Nov. 6, 2018, 30.8 KB], which is incorporated by reference herein. In the accompanying sequence listing:

SEQ ID NO: 1 is the amino acid sequence of a mSA2.

SEQ ID NO: 2 is the amino acid sequence of a mouse kappa immunoglobulin.

SEQ ID NO: 3 is the amino acid sequence of a human granulocyte-macrophage colony-stimulating factor (GM-CSF) receptor sequence.

SEQ ID NO: 4 is the amino acid sequence of a linker.

SEQ ID NO: 5 is the amino acid sequence of a CD8 hinge extracellular spacer domain.

SEQ ID NO: 6 is the amino acid sequence of a CD28 transmembrane.

SEQ ID NO: 7 is the amino acid sequence of a 4-1BB signaling domain.

SEQ ID NO: 8 is the amino acid sequence of a CD28 signaling domain.

SEQ ID NO: 9 is the amino acid sequence of a CD28 transmembrane domain and signaling domain.

SEQ ID NO: 10 is the amino acid sequence of a CD3 zeta signaling domain.

SEQ ID NO: 11 and 12 are amino acid sequences of exemplary CARs.

SEQ ID NO: 13 is a nucleic acid sequence encoding a signal sequence.

SEQ ID NO: 14 is a nucleic acid sequence encoding a mSA2.

SEQ ID NO: 15 is a nucleic acid sequence encoding a CD8 hinge.

SEQ ID NO: 16 is a nucleic acid sequence encoding a CD28 transmembrane domain.

SEQ ID NO: 17 is a nucleic acid sequence encoding a 4-1BB signaling domain.

SEQ ID NO: 18 is a nucleic acid sequence encoding a CD28 signaling domain.

SEQ ID NO: 19 is a nucleic acid sequence encoding CD3 zeta domain.

SEQ ID NO: 20 is a nucleic acid sequence encoding msa2-CD28ζ CAR.

SEQ ID NO: 21 is a nucleic acid sequence encoding msa2-41BBζ CAR, codon optimized for expression in humans.

SEQ ID NO: 22 is a nucleic acid sequence encoding a msa2-CD28ζ CAR, codon optimized for expression in humans.

SEQ ID NO: 23 is a nucleic acid sequence encoding a msa2-41Bbζ CAR, codon optimized for expression in humans.

SEQ ID NO: 24 is a nucleic acid sequence encoding a CAR, codon optimized for expression in humans, that was used as a control in the experimental studies.

DETAILED DESCRIPTION

A gene transfer system was produced and used to genetically engineer autologous T cells to express a chimeric antigen receptor (CAR) that binds to a "tag" such as a label. In some embodiments, the label is biotin. By combining the use of the CAR T cells with different biotinylated antibodies, one CAR can be used to target multiple different proteins, such as tumor proteins. In some embodiments, the disclosed CAR includes an affinity-enhanced streptavidin, such as, but not limited to, mSA2. The streptavidin can be monomeric. In some embodiments, the affinity-enhanced streptavidin can bind biotin with a 20-fold, 25-fold or 30-fold higher affinity than wild-type monomeric streptavidin. The use of the high affinity streptavidin, such as mSA2, results in increased killing, such as increased killing of tumor cells. Without being bound by theory, the use of the small mSA2, or high affinity variants thereof, is better suited to targeting larger tumor antigens, as compared to a scFv.

Terms

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Amino acid substitution: The replacement of one amino acid in peptide with a different amino acid.

Antibody: An immunoglobulin, antigen-binding fragment, or derivative thereof, that specifically binds and recognizes an analyte (antigen) such as a tumor associated antigen. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988; Ahmad et al., *Clin. Dev. Immunol.*, 2012, doi:10.1155/2012/980250; Marbry, *IDrugs*, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, $3^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally occurring immunoglobulin has two identical binding sites, a single-chain antibody or Fab fragment has one binding site, while a bispecific or bifunctional antibody has two different binding sites.

Typically, a naturally occurring immunoglobulin has heavy chains and light chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6$^{th}$ ed., W.H. Freeman and Co., page 91 (2007).) In several embodiments, the $V_H$ and $V_L$ combine to specifically bind the antigen. In additional embodiments, only the $V_H$ is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs can be referred to as LCDR1, LCDR2, and LCDR3. Heavy chain CDRs can be referred to as HCDR1, HCDR2, and HCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions, which have substantially no effect on antigen binding or other immunoglobulin functions. (See, for example, Harlow & Lane, Antibodies, A Laboratory Manual, 2$^{nd}$ ed. Cold Spring Harbor Publications, New York (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, and are typically of different species. In some examples, a chimeric antibody includes one or more CDRs and/or framework regions from one human antibody and CDRs and/or framework regions from another human antibody. In other embodiments, a chimeric antibody can include the VH and VL regions of a mouse monoclonal antibody (such as the 4A10 or 2B8 antibody) and human constant regions, such as human IgG1 regions.

A "fully human antibody" or "human antibody" is an antibody, which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1$^{st}$ Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

Aptamer: Oligonucleotide (nucleic acid aptamers) or peptide molecules that bind to a specific target molecule.

Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Exemplary nucleic acid aptamers that are known in the art can bind thrombin, hemin, interferon (IFN) y, vascular endothelial growth factor (VEGF), prostate specific antigen (PSA), and the oncogene heat shock factor 1 (HSF1).

Biological sample: A sample obtained from a subject. Biological samples include all clinical samples useful for detection of disease (for example, a tumor) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a tumor.

CD3 (Cluster of differentiation 3 T cell Co-receptor): A specific protein complex including at least four polypeptide chains, which are non-covalently associated with the T cell receptors on the surface of T cells. The four polypeptide chains include two CD3-epsilon chains, a CD3-delta chain and a CD3-gamma chain. CD3 is present on both helper T cells and cytotoxic T cells.

Chemotherapeutic agent: Any chemical agent with therapeutic usefulness in the treatment of diseases characterized by abnormal cell growth. For example, chemotherapeutic agents can be useful for the treatment of cancer, such as T-ALL or B-ALL. Particular examples of chemotherapeutic agents that can be used include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed.,© 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Williams & Wilkins, 2005; Skeel, *Handbook of Cancer Chemotherapy* (6th ed.). Lippincott Williams & Wilkins, 2003). Combination chemotherapy is the administration of more than one agent to treat cancer.

Chimeric Antigen Receptor (CAR): An engineered T cell receptor having an extracellular antigen binding domain joined to one or more intracellular signaling domains of a T cell receptor. A "chimeric antigen receptor T cell" is a T cell expressing a CAR, and has antigen specificity determined by the antibody-derived targeting domain of the CAR. Methods of making CARs are available (see, e.g., Park et al., *Trends Biotechnol.*, 29:550-557, 2011; Grupp et al., N Engl J Med., 368:1509-1518, 2013; Han et al., J. Hematol Oncol., 6:47, 2013; PCT Publication Nos. WO2012/079000, WO2013/059593; and U.S. Publication No. 2012/0213783, each of which is incorporated by reference herein in its entirety.)

Codon Optimized: A nucleic acid molecule encoding a protein can be codon optimized for expression of the protein in a particular organism by including the codon most likely to encode a particular amino acid with the amino acid sequence. Codon usage bias is the differences in the frequency of occurrence of synonymous codons (encoding the same amino acid) in coding DNA. A codon is a series of three nucleotides (a triplet) that encodes a specific amino acid residue in a polypeptide chain or for the termination of translation. There are 20 different naturally-occurring amino acids, but 64 different codons (61 codons encoding for amino acids plus 3 stop codons). Thus, there is degeneracy because one amino acid can be encoded by more than one codon. A nucleic acid sequence can be optimized for expression in a particular organism (such as a human) by evaluating the codon usage bias in that organism and selecting the codon most likely to encode a particular amino acid. Multivariate statistical methods, such as correspondence analysis and principal component analysis, are widely used to analyze variations in codon usage. Computer programs are available to implement the statistical analyses related to codon usage, such as Codon W, GCUA, and INCA.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane (*Antibodies, A Laboratory Manual*, $2^{nd}$ ed. Cold Spring Harbor Publications, New York, 2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Conservative variants: "Conservative" amino acid substitutions are those substitutions that do not substantially affect or decrease a function of a protein, such as the ability of the protein to interact with a target protein. For example, an IL-7Rα-specific antibody can include up to 1, 2, 3, 4, 5, 6, 7, 8, 9, or up to 10 conservative substitutions compared to a reference antibody sequence and retain specific binding activity for IL-7Rα. The term conservative variation also includes the use of a substituted amino acid in place of an unsubstituted parent amino acid.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function, such as for a tumor associated antigen-specific antibody, such as a CD20-specific antibody, the ability to specifically bind to the tumor associate antigen, such as CD20. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient that does not have a particular tumor. In other embodiments, the control is a positive control, such as a tissue sample obtained from a patient diagnosed with the tumor. In still other embodiments, the control is a historical control or standard reference value or range of values (such as a previously tested control sample, such as a group of patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Degenerate variant: In the context of the present disclosure, a "degenerate variant" refers to a polynucleotide encoding a protein (for example, a CAR)) that includes a sequence that is degenerate as a result of the genetic code. There are twenty natural amino acids, most of which are specified by more than one codon. Therefore, all degenerate nucleotide sequences are included as long as the amino acid sequence of the CAR encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something, such as the existence of a tumor. General methods of detecting are known to the skilled artisan and may be supplemented with the protocols and reagents disclosed herein.

Drug: Any compound used to treat, ameliorate or prevent a disease or condition in a subject. In some embodiments herein, the drug is a chemotherapeutic agent.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope of a tumor specific antigen.

Expression: Transcription or translation of a nucleic acid sequence. For example, a gene can be expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence, which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis- acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Fc polypeptide: The polypeptide including the constant region of an antibody excluding the first constant region immunoglobulin domain. Fc region generally refers to the last two constant region immunoglobulin domains of IgA, IgD, and IgG, and the last three constant region immunoglobulin domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region includes immunoglobulin domains Cgamma2 and Cgamma3 (Cγ2 and Cγ3) and the lower part of the hinge between Cgamma1 (Cγ1) and Cγ2. Although the boundaries of the Fc region may vary, the human IgG heavy chain Fc region is usually defined to include residues C226 or P230 to its carboxyl-terminus, wherein the numbering is according to the EU index as in Kabat. For IgA, the Fc region includes immunoglobulin domains Calpha2 and Calpha3 (Cα2 and Cα3) and the lower part of the hinge between Calpha1 (Cα1) and Cα2.

$K_D$: The dissociation constant for a given interaction, such as a polypeptide ligand interaction, streptavidin and biotin, or an antibody antigen interaction. For example, for the bimolecular interaction of an antibody or antigen binding fragment and an antigen is the concentration of the individual components of the bimolecular interaction divided by the concentration of the complex.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Linker: A bi-functional molecule that can be used to link two molecules into one contiguous molecule, for example, to link an effector molecule to an antibody. In some embodiments, the provided conjugates include a linker between the effector molecule or detectable marker and an antibody.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The nucleotides can be ribonucleotides, deoxyribonucleotides, or modified forms of either nucleotide. The term includes single- and double- stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences,* by E. W. Martin, Mack Publishing Co., Easton, Pa., 19th Edition, 1995, describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as on-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal end. In some embodiments, the polypeptide is a disclosed antibody or a fragment thereof.

Polypeptide modifications: Polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng and Doolittle, *J. Mol. Evol.* 35:351-360, 1987. The method used is similar to the method described by Higgins and Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff and Henikoff, *Proc. Natl. Acad. Sci. USA* 89:10915, 1989). An oligonucleotide is a linear polynucleotide sequence of up to about 100 nucleotide bases in length.

Signal Peptide: A short amino acid sequence (e.g., approximately 18-25 amino acids in length) that directs newly synthesized secretory or membrane proteins to and through membranes (for example, the endoplasmic reticulum membrane). Signal peptides are typically located at the N-terminus of a polypeptide and can be removed by signal peptidases after the polypeptide has crossed the membrane. Signal peptide sequences typically contain three common structural features: an N-terminal polar basic region (n-region), a hydrophobic core, and a hydrophilic c-region).

Specifically bind: A binding reaction which determines the presence of a target protein, peptide, or polysaccharide in the presence of a heterogeneous population of proteins and other biologics. Thus, under designated conditions, an antibody binds preferentially to a particular target protein, peptide or polysaccharide (such as a tumor associated antigen) and does not bind in a significant amount to other proteins or polysaccharides present in the sample or subject. Specific binding also occurs between streptavidin and biotin. Specific binding can be determined by methods known in the art.

With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar. The affinity of streptavidin for biotin is discussed below.

$K_D$ refers to the dissociation constant for a given interaction, such as a polypeptide ligand interaction or an antibody antigen interaction. For example, for the bimolecular interaction of an antibody or antigen binding fragment and an antigen it is the concentration of the individual components of the bimolecular interaction divided by the concentration of the complex.

The antibodies used in the methods disclosed herein specifically bind to a defined target, such as a tumor associated antigen. Thus, an antibody that specifically binds to an epitope on tumor associated antigen is an antibody that binds substantially to the tumor associated antigen, including cells or tissue expressing the tumor associated antigen. Streptavidin binds substantially to biotin. It is, of course, recognized that a certain degree of non-specific interaction may occur between an antibody or conjugate including an antibody (such as an antibody that specifically binds a tumor associated antigen or conjugate including such antibody) and a non-target (such as a cell that does not express the tumor associated antigen). Typically, specific binding results in a much stronger association between the antibody and protein or cells bearing the antigen than between the antibody and protein or cells lacking the antigen. Similarly, specific binding for streptavidin is between the streptavidin and biotin-labeled molecules (such as antibodies or aptamers), and not to molecules (such as antibodies or aptamers) labeled with a different marker. Specific binding typically results in greater than 2-fold, such as greater than 5-fold, greater than 10-fold, or greater than 100-fold increase in amount of bound antibody (per unit time) to a protein including the epitope (or labeled with biotin) or cell or tissue expressing the target epitope as compared to a protein lacking this epitope (or lacking biotin).

Subject: Living multi-cellular vertebrate organisms, a category that includes human and non-human mammals. In an example, a subject is a human. In a particular example, the subject is a pediatric subject, such as a human child age 2-5 years old. In an additional example, a subject is selected that has a tumor. In a further example, a subject is selected that has a solid tumor or is at risk of having a solid tumor.

T cell: A type of lymphocyte that plays a central role in cell-mediated immunity. T cells can be distinguished from other lymphocytes, such as B cells and natural killer cells, by the presence of a T-cell receptor on the cell surface. They are called T cells because they mature in the thymus from thymocytes. Generally, mature T cells express CD3.

T Cell Signaling Domain: An intracellular portion of a protein expressed in a T cell that transduces a T cell effector function signal (e.g., an activation signal) and directs the T cell to perform a specialized function. T cell activation can be induced by a number of factors, including binding of cognate antigen to the T cell receptor on the surface of T cells and binding of cognate ligand to co-stimulatory molecules on the surface of the T cell. A T cell co-stimulatory molecule is a cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor. Activation of a T cell leads to immune response, such as T cell proliferation and differentiation (see, e.g., Smith-Garvin et al., Annu. Rev. Immunol., 27:591-619, 2009). Exemplary T cell signaling domains are known and described herein. Non-limiting examples include the CD3 zeta, CD8, CD28, CD27, CD154, GITR (TNFRSF18), CD134 (OX40), and CD137 (4-1BB) signaling domains.

Therapeutically effective amount: The amount of an agent (such as a T cells and/or NK cells expressing a CAR) that alone, or together with one or more additional agents, such as an antibody that specifically binds a tumor associated antigen, induces the desired response, such as, for example treatment of a tumor in a subject. When administered to a subject, a dosage will generally be used that will achieve target tissue concentrations that has been shown to achieve a desired in vitro effect. Ideally, a therapeutically effective amount provides a therapeutic effect without causing a substantial cytotoxic effect in the subject.

In one example, a desired response is to decrease the size, volume, or number (such as metastases) of tumor cells in a subject, and/or neoplastic lesions or number of leukemia cells in blood in a subject. For example, the agent can decrease the size, volume, or number of tumor cells, and/or neoplastic lesions or number of leukemia cells in blood by a desired amount, for example by at least 5%, at least 10%, at least 15%, at least 20%, at least 25%, at least 30%, at least 50%, at least 75%, at least 90%, or at least 95% as compared to a response in the absence of the agent.

Several preparations disclosed herein are administered in therapeutically effective amounts. A therapeutically effective amount that is administered to a human or veterinary subject will vary depending upon a number of factors associated with that subject, for example the overall health of the subject. A therapeutically effective amount can be determined by varying the dosage and measuring the resulting therapeutic response, such as the regression of a tumor. Therapeutically effective amounts also can be determined through various in vitro, in vivo or in situ immunoassays. The disclosed agents can be administered in a single dose, or in several doses, as needed to obtain the desired response. However, the therapeutically effective amount of can be dependent on the source applied, the subject being treated, the severity and type of the condition being treated, and the manner of administration.

A therapeutically effective amount encompasses a fractional dose that contributes in combination with previous or subsequent administrations to attaining a therapeutic response. For example, a therapeutically effective amount of an agent can be administered in a single dose, or in several doses, for example daily, during a course of treatment lasting several days or weeks. However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Transduced and Transformed: A transformed cell is a cell into which a nucleic acid molecule has been introduced by molecular biology techniques. As used herein, the terms transduction and transformation encompass all techniques by which a nucleic acid molecule might be introduced into such a cell, including transfection with viral vectors, the use of plasmid vectors, and introduction of DNA by electroporation, lipofection, and particle gun acceleration.

Transmembrane domain: An amino acid sequence that inserts into a lipid bilayer, such as the lipid bilayer of a cell or virus or virus-like particle. A transmembrane domain can be used to anchor a protein of interest (such as a CAR) to a membrane. Exemplary transmembrane domains are familiar to the person of ordinary skill in the art, and provided herein.

Treating or Preventing a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as a tumor.

Tumor: An abnormal growth of cells, which can be benign or malignant (a malignancy). Cancer is a malignant tumor (a malignancy), which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma).

Tumor Associated Antigen: An antigenic substance produced in tumor cells that can trigger an immune response in the host or be bound by an antibody or aptamer. Tumor antigens are useful tumor markers in identifying tumor cells with diagnostic tests and are potential candidates for use in cancer therapy. Tumor associated antigens can be tumor specific, in that they are expressed by tumor cells but not normal cells.

Tumor burden: The total volume, number, metastasis, or combinations thereof of tumor or tumors in a subject.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

Chimeric Antigen Receptors

Chimeric antigen receptor (CARs) are disclosed that are artificially constructed chimeric proteins including an extracellular binding domain that specifically binds to a tag with a high affinity, linked to a transmembrane domain, and linked to one or more intracellular T cell signaling domains. In some embodiments, the tag is biotin, and the extracellular binding domain is a streptavidin, such as mSA2 or an amino acid sequence with at most five conservative amino acid substitutions that retains the binding affinity for biotin. Characteristics of the disclosed CARs include their ability to redirect T cell specificity and reactivity towards tumor cells expressing a tumor associated antigen, in a non-MHC-restricted manner. These tumor cells are contacted with a tumor specific binding agent, such as an antibody or an aptamer, covalently linked to the tag, such as biotin, wherein the binding agent specifically binds the tumor associated antigen. Upon binding to the biotinylated binding agent (such as the antibody or aptamer) the CAR T cell is activated, for example, the CAR T cell produces cytokines, and can lyse the tumor cells. The non-MHC-restricted recognition gives T cells (or NK cells) expressing a disclosed CAR the ability to recognize the tag, and is independent of antigen processing. T cells expressing the CAR thus can be used to target a wide variety of tumor types and tumor antigens. The only requirement to target a tumor is that there is a tumor specific binding agent, such as an aptamer or a monoclonal antibody that specifically binds the tumor cells. In some embodiments, a monoclonal antibody is utilized that specifically binds a tumor associated antigen. In some embodiments, mSA2 or a variant thereof is monomeric and has high affinity for biotin. The mSA2 or variant thereof itself has low immunogenicity, and thus can remain active for longer periods of time than other forms of streptavidin.

In some embodiments, the intracellular T cell signaling domains can include, for example, a T cell receptor signaling domain, a T cell costimulatory signaling domain, or both. The T cell receptor signaling domain refers to a portion of the CAR comprising the intracellular domain of a T cell receptor, such as the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen, such as 4-1BB or CD28. The CARs are disclosed in further detail below.

In some embodiments, the CAR includes: (a) an extracellular high affinity streptavidin, which can be monomeric or dimeric; (b) a hinge domain from CD8; (c) a CD28 transmembrane domain; (d) an intracellular 4-1BB and/or CD28 signaling domain; and (e) an intracellular CD3 zeta signaling domain, wherein (a)-(e) are in N-terminal to C-terminal order. In some embodiments, a signal sequence, such as but not limited to the mouse immunoglobulin signal sequence, is included N-terminal to the streptavidin, such as mSA2 or a variant thereof that includes at most 5 conservative amino acid substitutions and binds biotin with a high affinity.

A. Extracellular Region

The disclosed CARs include an extracellular binding domain that specifically binds to a tag with a high affinity, linked to a transmembrane domain, and linked to one or more intracellular T cell signaling domains. In some embodiments, the tag is biotin, and the extracellular binding domain is streptavidin. The streptavidin can be a monomeric streptavidin. In some embodiments, the monomeric streptavidin is mSA2 or an amino acid sequence with at most 5 conservative amino acid substitutions that retains the binding affinity for biotin.

The amino acid sequence of mSA2 is:

```
                                              (SEQ ID NO: 1)
GAEAGITGTWYNQHGSTFTVTAGADGNLTGQYENRAQGTGCQNSPYTLTG
RYNGTKLEWRVEWNNSTENCHSRTEWRGQYQGGAEARINTQWNLTYEGGS
GPATEQGQDTFTKVKPSAASGS
```

In some embodiments, the streptavidin is monomeric. In vivo, wild-type streptavidin forms a tetramer. The amino acid sequence shown above is primarily a monomer in vivo.

In some embodiments, at most 1, 2, 3, 4, 5, 6, 7, 8, 9, or 10 conservative substitutions can be introduced into SEQ ID NO: 1 and the monomeric form and the binding affinity can be retained. The essential domains of mSA2 are known, see Lim et al., Biotechnology Bioeng 110, 57-67, 2013, incorporated herein by reference. In some embodiments, the conservative substitutions, such as at most 1, 2, 3, 4 or 5 conservative substitutions, are made outside of the biotin binding pocket. Generally, the conservative substitutions do not change the binding affinity for the streptavidin for biotin. In some embodiments, the conservative substitutions do not change the monomeric form of the protein. In some embodiments, the amino acid substitutions can reduce the immunogenicity of the streptavidin. Suitable conservative substitutions include, but are not limited to, R103K, E101C, Y22S, see Yumura et al., Mutations for decreasing the immunogenicity and maintaining the function of core streptavidin. Protein Sci 2013; 22:213-21, incorporated herein by reference.

A high affinity avidin has a higher affinity for biotin than wild-type avidin. Wild-type monomer avidin has a $K_D$ for biotin of about $1 \times 10^{-4}$ at 37° C., see Urbanski et al., 2012, supra, and the wild-type dimer has an affinity of $1 \times 10^{-7}$ or less at 37° C., see Green and Toms, Biochem J 1973;133: 687-700; Laitinen et al., J Biol Chem 2001;276:8219-24.

In some embodiments, the streptavidin has a high affinity for biotin, and thus has a $K_D$ for biotin of greater than $1 \times 10^{-7}$ at 37° C., such as $1 \times 10^{-8}$ at 37° C. In some embodiments, the streptavidin has a high affinity for biotin, and has a $K_D$ for biotin of at least about $1 \times 10^{-9}$ at 37° C., at least about $2 \times 10^{-9}$ at 37° C., at least about $3 \times 10^{-9}$ at 37° C., at least about $4 \times 10^{-9}$ at 37° C., at least about $5 \times 10^{-9}$, or at least about $6 \times 10^{-9}$ at 37° C. at 37° C. In one specific non-limiting example, the streptavidin has a $K_D$ for biotin of at least about $5.5 \times 10^{-9}$ at 37° C. In other embodiments, the streptavidin has a $K_D$ for biotin of about $1 \times 10^{-9}$ at 37° C., about $2 \times 10^{-9}$ at 37° C., about $3 \times 10^{-9}$ at 37° C., about $4 \times 10^{-9}$ at 37° C., about $5 \times 10^{-9}$, or about $6 \times 10^{-9}$ at 37° C. at 37° C. In one specific non-limiting example, the streptavidin has a $K_D$ for biotin of about $5.5 \times 10^{-9}$ at 37° C. Thus, the streptavidin has a high affinity for biotin.

The CAR can include a signal peptide sequence, e.g., N-terminal to the antigen binding domain. The signal peptide sequence can include any suitable signal peptide sequence. In an embodiment, the signal peptide sequence is the mouse immunoglobulin light chain kappa signal sequence, such as an amino acid sequence including of consisting of METDTLLLWVLLLWVPGSTG (SEQ ID NO: 2). However, other signal sequences known in the art can be utilized. In another example, the signal peptide sequence is a human granulocyte-macrophage colony-stimulating factor (GM-CSF) receptor sequence, such as an amino acid sequence including or consisting of LLVTSLLL-CELPHPAFLLIPDT (SEQ ID NO: 3). In a further example, the signal peptide sequence is an IL-2 signal peptide. While the signal peptide sequence may facilitate expression of the CAR on the surface of the cell, the presence of the signal peptide sequence in an expressed CAR is not necessary in order for the CAR to function. Upon expression of the CAR on the cell surface, the signal peptide sequence may be cleaved off of the CAR. Accordingly, in some embodiments, the CAR lacks a signal peptide sequence.

Between the streptavidin and the transmembrane domain of the CAR, there can be a spacer domain, which includes a polypeptide sequence. The spacer domain may comprise up to 300 amino acids, such as 5 to 200 amino acids, such as 10 to 100 amino acids, for example 25 to 50 amino acids, SUCH AS 25, 26, 27, 28, 29 30, 31, 32, 33, 34, 35, 36, 37, 38, 39, 40, 41, 42, 43, 44, 45, 46, 47, 48, 49 or 50 amino acids. In some embodiments, the space domain is a human CD8 transmembrane domain, such as, but not limited to, SEQ ID NO: 5 (see below). In other embodiments, the spacer is omitted, so that it is not present.

B. Transmembrane Domain

With respect to the transmembrane domain, the CAR can be designed to include a transmembrane domain that is fused to the extracellular domain of the CAR. The transmembrane domain can be derived either from a natural or from a synthetic source. Where the source is natural, the domain can be from any membrane-bound or transmembrane protein. Exemplary transmembrane domains for use in the disclosed CARs can include at least the transmembrane region(s) of) the alpha, beta or zeta chain of the T cell receptor, CD28, CD3 epsilon, CD45, CD4, CD5, CD8, CD9, CD 16, CD22, CD33, CD37, CD64, CD80, CD86, CD 134, CD137, CD154.

Alternatively the transmembrane domain can be synthetic, in which case it will comprise predominantly hydrophobic residues such as leucine and valine. In several embodiments, a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the intracellular T cell signaling domain and/or T cell costimulatory domain of the CAR. An exemplary linker sequence includes one or more glycine-serine doublets. For example, the linker can include, or consist of:

```
                                                (SEQ ID NO: 4)
        SSGGGGSGGGGSGGGGS.
```

In some embodiments, the transmembrane domain comprises the transmembrane domain of a T cell receptor, such as a CD8 transmembrane domain. Thus, the CAR can include a CD8 transmembrane domain including or consisting of IYIWAPLAGTCGVLLLSLVITLYC (SEQ ID NO: 5).

In other embodiments, the transmembrane domain comprises the transmembrane domain of a T cell costimulatory molecule, such as CD137 or CD28. An exemplary CD28 transmembrane domain includes or consists of SEQ ID NO: 6:

```
        MFWVLVVVGGVLACYSLLVTVAFIIFWV.
```

C. Intracellular Region

The intracellular region of the CAR includes one or more intracellular T cell signaling domains responsible for activation of at least one of the normal effector functions of a T cell in which the CAR is expressed or placed in. Exemplary T cell signaling domains are provided herein, and are known to the person of ordinary skill in the art.

While an entire intracellular T cell signaling domain can be employed in a CAR, in many cases it is not necessary to use the entire chain. To the extent that a truncated portion of the intracellular T cell signaling domain is used, such truncated portion may be used in place of the intact chain as long as it transduces the relevant T cell effector function signal. Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

T cell receptor signaling domains regulate primary activation of the T cell receptor complex either in a stimulatory way, or in an inhibitory way. The disclosed CARs can include primary cytoplasmic signaling sequences that act in a stimulatory manner, which may contain signaling motifs that are known as immunoreceptor tyrosine-based activation motifs or ITAMs. Examples of ITAM containing primary cytoplasmic signaling sequences that can be included in a disclosed CAR include those from CD3 zeta, FcR gamma, FcR beta, CD3 gamma, CD3 delta, CD3 epsilon, CD5, CD22, CD79a, CD79b, and CD66d proteins. In several embodiments, the cytoplasmic signaling molecule in the CAR includes an intracellular T cell signaling domain from CD3 zeta.

The intracellular region of the CAR can include the ITAM containing primary cytoplasmic signaling domain (such as CD3-zeta) by itself or combined with any other desired cytoplasmic domain(s) useful in the context of a CAR. For example, the cytoplasmic domain of the CAR can include a CD3 zeta chain portion and an intracellular costimulatory signaling domain, such as, but not limited to, a 4-1BB (CD137) domain and/or a CD28 domain. The costimulatory signaling domain refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40 (CD134) CD30, CD40, PD-1, ICOS, lymphocyte function-associated antigen 1 (LFA-1), CD2, CD7, LIGHT, NKG2C, and B7-H3.

Exemplary amino acid sequences for such T cell signaling domains are provided. For example, a 4-1BB signaling domain includes of consists of the amino acid sequence set forth as:

```
                                                (SEQ ID NO: 7)
        KRGRKKLLYIFKQPFMRPVQTTQEEDG CSCRFPEEEEGGCEL.
```

A CD28 signaling domain can include or consists of:

```
                                                (SEQ ID NO: 8)
        SKRSRLLHSDYMNMTPRRPGPTRKHYQPYAPPRDFAAYRSGGG.
```

In some embodiments, both the CD28 transmembrane domain and signaling domains are utilized in the CAR:

```
                                                (SEQ ID NO: 9)
        IEVMYPPPYLDNEKSNGTIIHVKGKHLCPSPLFPGPSKPFWVLVVVGGVL
        ACYSLLVTVAFIIFWVRSKRSRLLHSDYMNMTPRRPGPTRKHYQPYAPPR
        DFAAYRSGGG.
```

In addition, a CD3 zeta signaling domain can be utilized. A CD3 zeta signaling domain can include or consist of the amino acid sequence set forth as:

```
                                                (SEQ ID NO: 10)
        RVKFSRSADAPAYQQGQNQLYNELN LGRREEYDVLDKRRGRDPEM
        GGKPRRKNPQEGLYNELQKD KMAEAYSEIGMKGERRRGKG
        HDGLYQGLSTATKDTYDALH MQALPPR.
```

The cytoplasmic signaling sequences within the cytoplasmic signaling portion of the CAR can be linked to each other in a random or specified order. In one non-limiting example, the 4-1BB domain/CD28 domain is included at the amino terminus of the CD3 zeta domain.

Optionally, a short polypeptide linker, preferably between 2 and 10 amino acids in length can form the linkage between these two domains. A glycine-serine doublet provides a particularly suitable linker. Further, between the signaling domain and the transmembrane domain of the CAR, there may be a spacer domain, which includes a polypeptide sequence. The spacer domain may include up to 300 amino acids, such as 10 to 100 amino acids, for example, 25 to 50 amino acids.

D. Additional Description of CARs

In some embodiments, the order of the domains is N-terminus, signal sequence, mSA2, hinge, transmembrane domain, human CD28 (and/or 4-1BB) signaling molecule, human CD3 zeta signaling molecule, C-terminus. An exemplary CAR of the present disclosure includes, or consists of, the amino acid sequence set forth as:

```
mSA2-41BBζCAR protein sequence (SEQ ID NO: 11)
METDTLLLWVLLLWVPGSTGGAEAGITGTWYNQHGSTFTVTAGADGNLTG

QYENRAQGTGCQNSPYTLTGRYNGTKLEWRVEWNNSTENCHSRTEWRG
```

```
-continued
QYQGGAEARINTQWNLTYEGGSGPATEQGQDTFTKVKPSAASGSTTTPAPR

PPTPAPTIASQPLSLRPEACRPAAGGAVHTRGLDFACD

MFWVLVVVGGVLACYSL

LVTVAFIIFWVKRGRKKLLYIFKQPFMRPVQTTQEEDGCSCRFP

EEEEGGCELRVKFSRSADAPAYQQGQNQLYNELNLGRREEYDVLDK

RRGRDPEMGGKPRRKNPQEGLYNELQKDKMAEAYSEIGMKGERRRGKGHD

GLYQGLSTATKDTYDALHMQALPPRLEGGGEGRGSLLTCGDVEENPG

PRMSELIKENMHMKLYMEGTVDNHHFKCTSEGEGKPYEGTQTMRIKVVEG

GPLPFAFDILATSFLYGSKTFINHTQGIPDFFKQSFPEGFTWERVTTY

EDGGVLTATQDTSLQDGCLIYNVKIRGVNFTSNG

PVMQKKTLGWEAFTETLYPADGGLEGRNDMAL

KLVGGSHLIANIKTTYRSKKPAKNLKMPGVYYVDYRLERIKE

ANNETYVEQHEVAVARYCDLPSKLGHKLN* mSA2-CD28ζCAR protein sequence (SEQ ID NO: 12)
METDTLLLWVLLLWVPGSTGGAEAGITGTWYNQHGSTFTVTAGADGNLTG

QYENRAQGTGCQNSPYTLTGRYNGTKLEWRVEWNNSTENCHSRTEWRG

QYQGGAEARINTQWNLTYEGGSGPATEQGQDTFTKVKPSAASGSTTT

PAPRPPTPAPTIASQPLSLRPEACRPAAGGAVHTRGLDFACD

MFWVLVVVGGVLACYSL

LVTVAFIIFWVRSKRSRGGHSDYMNMTPRR

PGPTRKHYQPYAPPRDFAAYRSGGGR

VKFSRSADAPAYQQGQNQLYNELNLGRREEYDVLDKRRGRDPE

MGGKPRRKNPQEGLYNELQKDKMAEAYSEIGMKGERRRGKGHDGLYQGL

STATKDTYDALHMQALPPRLEGGGEGRGSLLTCGDVEENPGPRMSELIK

ENMHMKLYMEGTVDNHHFKCTSEGEGKPYEGTQTMRIKVVEGGPLPFAF

DILATSFLYGSKTFINHTQGIPDFFKQSFPEGFTWERVTTYED

GGVLTATQDTSLQDGCLIYNVKIRGVNFTSNGPVMQKKT

LGWEAFTETLYPADGGLEGRNDMALKLVGGSHLIANIKTTYRSKKPAKN

LKMPGVYYVDYRLERIKEANNETYVEQHEVAVARYCDLPSKLGHKLN*
Code:
Leader sequence: Underline
msa2: Bold
CD8hinge: Double underline
CD28-TM,cyto : Italics
CD3zeta: Dashed underline
T2A-TagBFP: None
4-1BB: Arial font and jagged underline
```

Also provided are functional portions of any of the CARs described herein. The term "functional portion" when used in reference to a CAR refers to any part or fragment of the CAR, which part or fragment retains the biological activity of the CAR of which it is a part (the parent CAR), and thus can be used to target T cells and/or natural killer cells to biotinylated molecules. Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 60%, 70%, 80%, 90%, 95%, 965, 97%, 98% or more, of the parent CAR.

The CAR or functional portion thereof, can include additional amino acids at the amino or carboxy terminus, or at both termini, which additional amino acids are not found in the amino acid sequence of the parent CAR. In some examples, the additional amino acids do not interfere with the biological function of the CAR or functional portion, e.g., recognize target cells, detect cancer, treat or prevent cancer, etc. In other examples, the additional amino acids enhance the biological activity, as compared to the biological activity of the parent CAR.

Also provided are functional variants of the CARs described herein, which have substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, the non-conservative amino acid substitution does not interfere with or inhibit the biological activity of the functional variant. The non-conservative amino acid substitution may enhance the biological activity of the functional variant, such that the biological activity of the functional variant is increased as compared to the parent CAR. The CAR can also include up to ten conservative amino acid substitutions, such as 1, 2, 3, 4, 5, 6, 7, 8, 9, or 10 conservative substitutions, provided the activity of the molecule is not changed. Substitutions can be made, for example, in the linker region, spacers, and/or the signal sequence.

The CARs (including functional portions and functional variants of the invention) can include synthetic amino acids in place of one or more naturally-occurring amino acids. Such synthetic amino acids are known in the art, and include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, -(2-amino-2-norbornane)-carboxylic acid, γ-diaminobutyric acid, α,β-diaminopropionic acid, homophenylalanine, and α-tert-butylglycine. The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

Methods of generating chimeric antigen receptors, immune cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online February 23, 2010, pages 1-9; Till et al., 2008, Blood, 1 12:2261 -2271; Park et al., Trends Biotechnol., 29:550-557, 2011; Grupp et al., N Engl J Med., 368:1509-1518, 2013; Han et al., J. Hematol Oncol., 6:47, 2013; PCT Publication Nos. WO2012/079000, WO2013/126726; and U.S. Publication No. 2012/0213783, each of which is incorporated by reference herein in its entirety). For example, a nucleic acid molecule encoding a disclosed chimeric antigen binding receptor can be included in an expression vector (such as a lentiviral vector) for expression in a host cell, such as a T cell, to make the disclosed CAR. In some embodiments, methods of using the chimeric antigen receptor include isolating T cells from a subject, transforming the T cells with an expression vector (such as a lentiviral vector or a gamma retroviral vector) encoding the chimeric antigen receptor, and administering the engineered T cells expressing the chimeric antigen receptor to the subject for treatment, for example for treatment of a cancer in the subject.

Polynucleotides and Expression

Nucleic acid molecules (for example, cDNA molecules) encoding the amino acid sequences of CARs, such as, but not limited to, mSA2 biotin-binding CARs, are provided herein. Nucleic acids encoding these molecules can readily be produced by one of skill in the art, using the amino acid sequences provided herein, sequences available in the art (such as linker, CD8, CD28 and 4-1BB sequences), and the genetic code. In several embodiments, the nucleic acid molecules can be expressed in a host cell (such as a mammalian cell, for example a T cell) to produce the CAR. The nucleic acid molecules can be codon-optimized for expression in humans.

In some embodiments, the complete nucleic acid sequence encoding the CAR is codon optimized for expression in human cells, such as human T cells or natural killer (NK) cells. In additional embodiments, a nucleic acid sequence encoding one or more components of the CAR (biotin binding (e.g., mSA2), signal sequence, human CD8 hinge domain, human CD28 transmembrane domain, human 4-1BB or CD28 signaling molecule, human CD3 zeta signaling molecule) can be codon optimized for expression in human cells, but all of the nucleic acid sequences encoding the components of the CAR are codon optimized for expression in human cells. Thus, in some embodiments, the nucleic acid sequence includes one or more codon optimized nucleic acid sequences.

In some embodiments, the nucleic acid sequence encoding the signal sequence, for example the mouse immunoglobulin light chain kappa signal sequence, is codon optimized for expression in human cells. In one non-limiting example, the nucleic acid molecule encoding the signal sequence can include, or consist of:

(SEQ ID NO: 13)
ATGGAGACAGACACACTCCTGCTATGGGTGCTGCTGCTCTGGGTTCCAGG
TTCCACAGGT.

In other embodiments, the nucleic acid molecule encoding the signal sequence in the CAR includes a nucleic acid encoding a signal sequence at least 80%, 85%, 90%, 95%, 96%, 97%, 98%, or 99% identical to SEQ ID NO: 13, wherein the sequence functions as a signal sequence in human cells, such as human T cells and/or NK cells.

In further embodiments, the nucleic acid sequence encoding the extracellular high affinity streptavidin is codon optimized for expression in human cells. In some embodiments, the extracellular high affinity streptavidin is mSA2. In more embodiments, the nucleic acid encoding mSA2 is codon optimized for expression in human cells. In a non-limiting example, the nucleic acid encoding the mSA2 of the CAR can include, or consist of SEQ ID NO: 14:

GCGCAGAGGCGGGTATCACCGGGACATGGTACAACCAACACGGAAGCACA

TTTACAGTCACCGCTGGAGCAGACGGGAATCTGACCGGACAGTACGAGAA

CAGGGCTCAGGGGACAGGTTGTCAGAACAGTCCGTATACTCTGACTGGGA

GGTACAATGGCACGAAGCTGGAGTGGCGAGTCGAGTGGAATAATTCCACG

GAAAACTGTCACAGTAGAACAGAGTGGAGGGGACAGTACCAGGGGGAGC

AGAGGCCCGGATCAACACCCAATGGAACTTGACATATGAAGGCGGGTCAG

GCCCCGCGACAGAGCAAGGACAGGATACATTCACGAAGGTCAAGCCAAGC

GCAGCCTCTGGCTCT

In other embodiments, the nucleic acid molecule encoding the CAR includes a nucleic acid sequence encoding a mSA2 at least 90%, 95%, 96%, 97%, 98%, or 99% identical to SEQ ID NO: 14, wherein the encoded protein specifically binds biotin.

In more embodiments, the nucleic acid sequence encoding the human CD8 hinge can be codon optimized for expression in human cells. In one non-limiting example, the nucleic acid encoding the CD8 hinge in the CAR can include, or consist of:

(SEQ ID NO: 15)
ACCACAACTCCAGCTCCCCGGCCCCCTACTCCTGCTCCAACCATTGCCTC
ACAGCCACTGAGCCTGCGGCCCGAAGCTTGTAGACCTGCTGCTGGAGGAG
CTGTGCATACCAGAGGCCTGGACTTCGCCTGCGAT.

In other embodiments, the nucleic acid molecule encoding the CAR includes a nucleic acid sequence encoding a CD8 hinge is at least 80%, 85%, 90%, 95%, 96%, 97%, 98%, or 99% identical to SEQ ID NO: 15, wherein the encoded protein functions as a hinge domain.

In more embodiments, the nucleic acid sequence encoding the human CD28 hinge can be codon optimized for expression in human cells. In further embodiments, the nucleic acid sequence encoding the CD28 transmembrane domain is
ATGTTCTGGGTGCTGGTGGTGGTGGGCGGGGTG-CTGGCCTGCTACAGCCTGCTGGTGACAGTG GCCTTCATCATCTTTTGGGTG (SEQ ID NO: 16). In other embodiments, the nucleic acid molecule encoding the CAR includes a nucleic acid sequence encoding a CD28 transmembrane domain is at least 80%, 85%, 90%, 95%, 96%, 97%, 98%, or 99% identical to SEQ ID NO: 16, wherein the encoded protein functions as a transmembrane domain. The sequence can be codon optimized for expression in human cells.

In some embodiments, the CAR can includes the 4-1BB domain. Thus, the nucleic acid sequence encoding the human 4-1BB signaling molecule can be codon optimized for expression in human cells. Thus, the nucleic acid encoding the 4-1BB signaling molecule in the CAR can include, or consist of:

(SEQ ID NO: 17)
AAACGGGGCAGAAAGAAACTCCTGTATATATTCAAACAACCATTTATGAG
ACCAGTACAAACTACTCAAGAGGAAGATGGCTGTAGCTGCCGATTTCCAG
AAGAAGAAGAAGGAGGATGTGAACTG.

In other embodiments, the nucleic acid molecule encoding the CAR includes a nucleic acid sequence encoding a 4-1BB signaling molecule is at least 85%, 90%, 95%, 96%, 97%, 98%, or 99% identical to SEQ ID NO: 17, wherein the encoding protein functions as a signaling molecule.

In further embodiments, the CAR can include the CD28 signaling domain. In some non-limiting examples, the nucleic acid sequence encoding the CD28 signaling molecule can be codon optimized for expression in human cells. In additional non-limiting examples, the nucleic acid encoding the CD28 signaling molecule in the CAR can include, or consist of:

(SEQ ID NO: 18)
CGGAGCAAGCGGAGCAGAGGCGGCCACAGCGACTACATGAACATGACCCC
CAGACGGCCTGGCCCCACCCGGAAGCACTACCAGCCCTACGCCCCACCCA
GGGACTTTGCCGCCTACCGGTCCGGCGGAGGG

In other embodiments, the nucleic acid molecule encoding the CAR includes a nucleic acid sequence encoding a CD28 signaling molecule is at least 85%, 90%, 95%, 96%, 97%, 98%, or 99% identical to SEQ ID NO: 18, wherein the encoding protein functions as a signaling molecule.

In additional embodiments, the nucleic acid sequence encoding the CD3 zeta domain can be codon optimized for expression in human cells. Thus, the nucleic acid encoding the CD3 zeta domain in the CAR can include, or consist of:

(SEQ ID NO: 19)
CGGGTGAAGTTCAGCAGAAGCGCCGACGCCCCTGCCTACCAGCAGGGCCA
GAATCAGCTGTACAACGAGCTGAACCTGGGCAGAAGGGAAGAGTACGACG
TCCTGGATAAGCGGAGAGGCCGGGACCCTGAGATGGGCGGCAAGCCTCGG
CGGAAGAACCCCCAGGAAGGCCTGTATAACGAACTGCAGAAAGACAAGAT
GGCCGAGGCCTACAGCGAGATCGGCATGAAGGGCGAGCGGAGGCGGGGCA
AGGGCCACGACGGCCTGTATCAGGGCCTGTCCACCGCCACCAAGGATACC
TACGACGCCCTGCACATGCAGGCCCTGCCCCCAAGG.

In other embodiments, the nucleic acid molecule encoding the CAR includes a nucleic acid sequence encoding a CD3 zeta signaling molecule is at least 80%, 85%, 90%, 95%, 96%, 97%, 98%, or 99% identical to SEQ ID NO: 17, wherein the encoded protein functions as a CD3 zeta signaling molecule.

In one specific non-limiting example, the entire nucleic acid sequence encoding the CAR comprises, or consists of:

msa2-CD28ζCAR DNA sequence (SEQ ID NO: 20):
ATGGAGACAGACACACTCCTGCTATGGGTGCTGCTGCTCTGGGTTCC

AGGTTCCACAGGTGGCGCAGAGGCGGGTATCACCGGGACAT

GGTACAACCAAC

ACGGAAGCACATTTACAGTCACCGCTGGAGCAGACGGGAATCTGACCG

GACAGTACGAGAACAGGGCTCAGGGGACAGGTTGTCAGAACAGTCCGT

ATACTCTGACTGGGAGGTACAATGGCACGAAGCTGGAGTGGCGAGTCG

AGTGGAATAATTCCACGGAAAACTGTCACAGTAGAACAGAGTGGAGGG

GACAGTACCAGGGGGGAGCAGAGGCCCGGATCAACACCCAATGAACT

TGACATATGAAGGCGGGTCAGGCCCCGCGACAGAGCAAGGACAGGATA

CATTCACGAAGGTCAAGCCAAGCGCAGCCTCTGGCTCTACCACAACTCC

AGCTCCCCGGCCCCTACTCCTGCTCCAACCATTGCCTCACAGCCACTG

AGCCTGCGGCCCGAAGCTTGTAGACCTGCTGCTGGAGGAGCTGTGCATAC

CGGCCTGGACTTCGCCTGCGATATGTTCTGGGTGCTGGTGGTGGT

GGGCGGGGTGCTGGCCTGCTACAGCCTGCTGGTGACAGTGGCC

TTCATCATCTTTTGGGTGCGGAGCAAGCGGAGCAGAGGCGGCCACA

GCGACTACATGAACATGACCCCCAGACGGCCTGGCCCCACCC

GGAAGCACTACCAGCCCTACGCCCCACCCAGGGAACTTT

GCCGCCTACCGGTCCGGCGGAGGG

CGGGTGAAGTTCAGCAGAAGCGCCGAC
-----------------------------------

GCCCCTGCCTACCAGCAGGGCCAGAATCAGCTGTACAACGAGCTGAACCTG
-----------------------------------------------------------

GGCAGAAGGGAAGAGTACGACGTCCTGGATAAGCGGAGAGGCCGGGACCC
-----------------------------------------------------------

TGAGATGGGCGGCAAGCCTCGGCGGAAGAACCCCCAGGAAGGCCTGTATA
-----------------------------------------------------------

ACGAACTGCAGAAAGACAAGATGGCCGAGGCCTACAGCGAGATCGGCATG
-----------------------------------------------------------

AAGGGCGAGCGGAGGCGGGGCAAGGGCCACGACGGCCTGTATCAGGGCCT
-----------------------------------------------------------

GTCCACCGCCACCAAGGATACCTACGACGCCCTGCACATGCAGGCCCTGCC
-----------------------------------------------------------

CCCAAGG
--------- msa2-41BBζCAR DNA sequence (SEQ ID NO: 21):
ATGGAGACAGACACACTCCTGCTATGGGTGCTGCTGCTCTGGGTTCCAG

GTTCCACAGGTGGCGCAGAGGCGGGTATCACCGGGACATGGTACAACCAA

CACGGAAGCACATTTACAGTCACCGCTGGAGCAGACGGGAATCTGACCG

GACAGTACGAGAACAGGGCTCAGGGGACAGGTTGTCAGAACAGTCCGT

ATACTCTGACTGGGAGGTACAATGGCACGAAGCTGGAGTGGCGAGTCG

AGTGGAATAATTCCACGGAAAACTGTCACAGTAGAACAGAGTGGAGGG

GACAGTACCAGGGGGGAGCAGAGGCCCGGATCAACACCCAATGAACT

TGACATATGAAGGCGGGTCAGGCCCCGCGACAGAGCAAGGACAGGATA

CATTCACGAAGGTCAAGCCAAGCGCAGCCTCTGGCTCTACCACAACTCC

AGCTCCCCGGCCCCTACTCCTGCTCCAACCATTGCCTCACAGCCACT

```
-continued
GAGCCTGCGGCCCGAAGCTTGTAGACCTGCTGCTGGAGGAGCTGTGCA

TACCAGAGGCCTGGACTTCGCCTGCGATATGTTCTGGGTGCTGGTGG

TGGTGGGCGGGGTGCTGGCCTGCTACAGCCTGCTGGTGAC

AGTGGCCTTCATCATCTTTTGGGTGAAACGGGGCAGAA

AGAAACTCCTGTATATATTCAAACAACCATTTATGAGACC

AGTACAAACTACTCAAGAGGAAGATGGCTGTAGCTGCCGATTTCCAGAAG

AAGAAGAAGGAGGATGTGAACTGCGGGTGAAGTTCAGCAGAA

GCGCCGACGCCCCTGCCTACCAGCAGGGCCAGAATCAGCTGTACAA

CGAGCTGAACCTGGGCAGAAGGGAAGAGTACGACGTCCTGGATAA

GCGGAGAGGCCGGGACCCTGAGATGGCGGCAAGCCTCGGCGG

AAGAACCCCCAGGAAGGCCTGTATAACGAACTGCAGAAAGACAAGA

TGGCCGAGGCCTACAGCGAGATCGGCATGAAGGGCGAGCGGAGGCGGG

GCAAGGGCCACGACGGCCTGTATCAGGGCCTGTCCACCGCCACC

AAGGATACCTACGACGCCCTGCACATGCAGGCCCTGCCCCCAAGG
Code:
Leader sequence: Underline
mSA2: Bold
CD8αhinge: Double underline
CD28-TM,cyto: Italics
CD3zeta: Dashed underline
4-1BB: Arial font
```

Exemplary constructs including these sequence are shown in FIGS. 7A-7D, see SEQ ID NOs: 23 and 24. Nucleic acid sequences encoding the antibodies, antibody binding fragments, CARs and conjugates that specifically bind biotin can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, 4th ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill. Modifications can be made to a nucleic acid encoding a polypeptide described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the CARs of the present disclosure can also be constructed in whole or in part using standard peptide synthesis well known in the art.

The nucleic acid molecule encoding the chimeric antigen binding receptor can operably linked to a promoter. The nucleic acid molecule encoding the CAR can be included in a vector (such as a lentiviral vector or gamma retroviral vector) for expression in a host cell. Exemplary cells are mammalian cells, and include a T cell, such as a cytotoxic T lymphocyte (CTL) or a regulatory T cell, and a NK cell. In specific non-limiting examples, the cell is a T cell, such as a CD3[+] T cell. The CD3[+] T cell can be a CD4[+] or a CD8[+] T cell. In other specific non-limiting examples, the cell is a NK cell. Methods of generating nucleic acid molecules encoding chimeric antigen receptors and T cells (or NK cells) including such receptors are known in the art (see, e.g., Brentjens et al., 2010, Molecular Therapy, 18:4, 666-668; Morgan et al., 2010, Molecular Therapy, published online Feb. 23, 2010, pages 1 -9; Till et al., 2008, Blood, 1 12:2261 -2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety).

If of interest, once expressed, a CAR can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin. Additional methods for expression and purification are known in the art, see, e.g., Harlow and Lane, *Antibodies: A Laboratory Manual*, 2nd, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

The nucleic acid molecules also can be expressed in a recombinantly engineered cell such as bacteria, plant, yeast, insect and mammalian cells. The CAR can be expressed as a fusion protein. Methods of expressing and purifying antibodies and antigen binding fragments are known and further described herein (see, e.g., Al-Rubeai (ed), *Antibody Expression and Production*, Springer Press, 2011). Those of skill in the art are knowledgeable in the numerous expression systems available for expression of proteins including *E. coli,* other bacterial hosts, yeast, and various higher eukaryotic cells such as the COS, CHO, HeLa and myeloma cell lines. The term "host cell" also includes any progeny of the subject host cell. It is understood that all progeny may not be identical to the parental cell since there may be mutations that occur during replication. Methods of stable transfer, meaning that the foreign DNA is continuously maintained in the host, are known in the art. As disclosed herein, specific embodiments of the present disclosure include T cells, such as human T cells and human NK cells, which express the CAR. These T cells can be $CD3^+$ T cells, such as $CD4^+$ or $CD8^+$ T cells. If of interest, once expressed, a CAR can be purified according to standard procedures in the art, including ammonium sulfate precipitation, affinity columns, column chromatography, and the like (see, generally, Simpson ed., Basic methods in Protein Purification and Analysis: A laboratory Manual, Cold Harbor Press, 2008). The antibodies, antigen binding fragment, and conjugates need not be 100% pure. Once purified, partially or to homogeneity as desired, if to be used therapeutically, the polypeptides should be substantially free of endotoxin. Additional methods for expression and purification are known in the art, see, e.g., Harlow and Lane, *Antibodies: A Laboratory Manual,* $2^{nd}$, Cold Spring Harbor Laboratory, New York, 2013, Simpson ed., Basic methods in Protein Purification and Analysis: A laboratory Manual, Cold Harbor Press, 2008, and Ward et al., *Nature* 341:544, 1989.

The expression of nucleic acids encoding the antibodies and antigen binding fragments described herein can be achieved by operably linking the DNA encoding the CAR to a promoter (which is either constitutive or inducible), followed by incorporation into an expression cassette. The promoter can be any promoter of interest, including a cytomegalovirus promoter and a human T cell lymphotrophic virus promoter (HTLV)-1. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, at the minimum, a strong promoter to direct transcription, a ribosome binding site for translational initiation (internal ribosomal binding sequences), and a transcription/translation terminator. For *E. coli,* this can include a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the CAR, and a second foreign DNA molecule encoding a selectable phenotype, such as the herpes simplex thymidine kinase gene. Another method is to use a eukaryotic viral vector, such as simian virus 40 (SV40), a lentivirus or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In some embodiments, a viral vector is utilized for expression of the CAR. Viral vectors include, but are not limited to simian virus 40, adenoviruses, adeno-associated virus (AAV), lentiviral vectors, and retroviruses, such as gamma retroviruses. Retroviral vectors provide a highly efficient method for gene transfer into eukaryotic cells. Moreover, retroviral integration takes place in a controlled fashion and results in the stable integration of one or a few copies of the new genetic information per cell. Without being bound by theory, lentiviral vectors have the advantage over vectors derived from onco-retroviruses such as murine leukemia viruses in that they can transduce non-proliferating cells, such as hepatocytes. They also have the added advantage of low immunogenicity. The use of lentiviral vectors to express a CAR is known in the art, and is disclosed for example in U.S. Application No. 2014/0050708, which is incorporated herein by reference.

In some embodiments, host cells are produced for introduction into s subject of interest. The host cell can be a peripheral blood lymphocyte (PBL) or a peripheral blood mononuclear cell (PBMC), a purified T cell, or a purified NK cell. The T cell can be any T cell, such as a cultured T cell, e.g., a primary T cell, or a T cell from a cultured T cell line, e.g., Jurkat, SupT1, etc., or a T cell obtained from a mammal (such as a human patient to which the CAR-T cell will later be administered). If obtained from a mammalian subject, such as a human subject, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, $CD3^+$ cells, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naive T cells, and the like.

The T cell may be a CD3+ T cell, such as a CD8+ T cell or a CD4+ T cell. In alternative embodiments, the cell can be an NK cells, such as an NK cell obtained from the same subject to which the CAR-NK cell will later be administered.

Also provided is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any recombinant expression vector, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector encoding the CAR. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein. The T cells can be CD3+ T cells, such as CD8+ T cell or a CD4+ T cells. In some embodiments, the T cells are transformed with Epstein Barr virus, see Savoldo et al., Blood 110: 2620-2630, 2007, incorporated herein by reference. In other embodiments, the cells are heterologous to a recipient (see below), and are deleted for a HLA class I and/or T cell receptor, so they do not provoke a graft versus host disease (GVHD) or host versus graft reaction. The cells can also be NK cells. The cells can be autologous to a recipient or allogeneic. These populations are of use in any of the methods disclosed herein.

Methods of Treatment and Pharmaceutical Compositions

Disclosed herein are methods for treating a tumor. The method includes administering to the subject a therapeutically effective amount of an antibody or aptamer that specifically binds a tumor associated antigen expressed by the tumor, wherein the antibody or aptamer is biotinylated, and administering to the subject a therapeutically effective amount of the pharmaceutical composition including a vector, such as a lentiviral vector encoding the CAR, and/or administering a therapeutically effective amount of a pharmaceutical composition comprising cells, such as T cells and/or NK cells, that express the CAR disclosed above.

Pharmaceutical compositions can include a CAR-expressing cell, e.g., a plurality of CAR-expressing cells, as described herein, in combination with one or more pharmaceutically or physiologically acceptable carriers, diluents or excipients. The CAR-expressing cells can be T cells, such as CD3+ T cells, such as CD4+ and/or CD8+ T cells, and/or NK cells. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The cells can be autologous to the recipient. However, the cells can also be heterologous (allogeneic). In some embodiments, the cells are T cells, such as T cells transformed with Epstein Barr virus, see Savoldo et al., Blood 110: 2620-2630, 2007, incorporated herein by reference. In other embodiments, the cells are heterologous (allogeneic) to a recipient (see below), and are deleted for a HLA class I and/or T cell receptor, so they do not provoke a graft versus host disease (GVHD) or host versus graft reaction.

With regard to the cells, a variety of aqueous carriers can be used, for example, buffered saline and the like, for introducing the cells. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration in these formulations can vary widely, and will be selected primarily based on fluid volumes, viscosities, body weight and the like in accordance with the particular mode of administration selected and the subject's needs.

In one embodiment, the pharmaceutical composition is substantially free of, e.g., there are no detectable levels of a contaminant, such as endotoxin, mycoplasma, replication competent lentivirus (RCL), residual anti-CD3/anti-CD28 coated beads, mouse antibodies, pooled human serum, bovine serum albumin, bovine serum, culture media components, vector packaging cell or plasmid components, a bacterium and a fungus.

The precise amount of the composition to be administered can be determined by a physician with consideration of individual differences in age, weight, tumor size, extent of metastasis, and condition of the patient (subject). It can generally be stated that a pharmaceutical composition comprising the T cells (and/or NK cells) described herein may be administered at a dosage of $10^4$ to $10^9$ cells/kg body weight, such as $10^5$ to $10^6$ cells/kg body weight, including all integer values within those ranges. Exemplary doses are $10^6$ cells/kg to about $1 \times 10^8$ cells/kg, such as from about $5 \times 10^6$ cells/kg to about $7.5 \times 10^7$ cells/kg, such as at about $2.5 \times 10^7$ cells/kg, or at about $5.0 \times 10^7$ cells/kg.

A composition can be administered once or multiple times, such as 2, 3,4, 5, 6, 7, 8, 9, or 10 times at these dosages. The composition can be administered by using infusion techniques that are commonly known in immunotherapy (see, e.g., Rosenberg et al., New Eng. J. of Med. 319:1676, 1988). The compositions can be administered daily, weekly, bimonthly or monthly. In some non-limiting examples, the composition is formulated for intravenous administration and is administered multiple times. The quantity and frequency of administration will be determined by such factors as the condition of the subject, and the type and severity of the subject's disease, although appropriate dosages may be determined by clinical trials.

In one embodiment, the CAR is introduced into cells, such T cells or NK cells, and the subject receives an initial administration of cells, and one or more subsequent administrations of the cells, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the CAR cells are administered to the subject (e.g., human) per week, e.g., 2, 3, or 4 administrations of the CAR cells of the invention are administered per week. In one embodiment, the subject receives more than one administration of the CAR T cells per week (e.g., 2, 3 or 4 administrations per week) (also referred to as a cycle), followed by a week of no CAR cells administrations, and then one or more additional administration of the CAR cells (e.g., more than one administration of the CAR T cells per week) is administered to the subject. In another embodiment, the subject (e.g., human subject) receives more than one cycle of CAR cells, and the time between each cycle is less than 10, 9, 8, 7, 6, 5, 4, or 3 days. In one embodiment, the CAR cells are administered every other day for 3 administrations per week. In another embodiment, the CAR cells are administered for at least two, three, four, five, six, seven, eight or more weeks. The dosage of the above treatments to be administered to a patient will vary with the precise nature of the condition being treated and the recipient of the treatment. The scaling of dosages for human administration can be performed according to art-accepted practices.

In some embodiments, CAI modified T cells are able to replicate in vivo resulting in long-term persistence that can lead to sustained tumor control. In various aspects, the T cells administered to the subject, or the progeny of these cells, persist in the subject for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, or for years after administration of the T cell to the subject. In other embodiments, the cells and their progeny are present for less than six months, five month, four months, three months two months, or one month, e.g., three weeks, two weeks, one week, after administration of the T cell to the subject.

The administration of the subject compositions may be carried out in any convenient manner, including by injection, ingestion, transfusion, implantation or transplantation. The disclosed compositions can be administered to a patient trans arterially, subcutaneously, intradermally, intratumorally, intranodally, intramedullary, intramuscularly, by intravenous (i.v.) injection, or intraperitoneally. In some embodiments, the compositions are administered to a patient by intradermal or subcutaneous injection. In other embodiments, the compositions of the present invention are administered by i.v. injection. The compositions can also be injected directly into a tumor or lymph node.

In some embodiments, subjects can undergo leukapheresis, wherein leukocytes are collected, enriched, or depleted ex vivo to select and/or isolate the cells of interest, e.g., T cells and or NK cells. These cell isolates may be expanded by methods known in the art and treated such that one or more CAR constructs can be introduced, thereby creating an autologous cell that express the CAR. In one aspect, CAR expressing cells are generated using lentiviral viral vectors.

In some embodiments, the T and/or NK cells are autologous. In other embodiments, the T cells and/or NK cells are allogeneic. The T calls and/or NK cells are then introduced into the subject, as disclosed above. In one embodiment, the cells transiently express the vector for 4, 5, 6, 7, 8, 9, 10, 11, 12, 13, 14, 15 days after transduction. In one non-limiting example, the vector is transduced into the T cell by electroporation.

In some embodiments, a subject is administered a therapeutically effective amount of T cells and/or NK cells expressing the disclosed CAR. In particular embodiments (see U.S. Published Application No. US20140271635 A1, incorporated herein by reference), prior to expansion and genetic modification, a source of T cells is obtained from a subject.

The term "subject" is intended to include living organisms in which an immune response can be elicited (e.g., mammals). Examples of subjects include humans, dogs, cats, mice, rats, pigs (and other veterinary subjects) and non-human primates. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In other embodiments, any number of T cell lines available in the art, may be used. In some non-limiting examples, T cells and/or NK cells can be obtained from a unit of blood collected from a subject using any number of techniques known to the skilled artisan, such as FICOLL™ separation, or the cells can be obtained by apheresis. The apheresis product typically contains lymphocytes, including T cells, monocytes, granulocytes, B cells, NK cells, other nucleated white blood cells, red blood cells, and platelets. In some specific non-limiting examples, the cells are autologous.

Cells collected by apheresis can be washed to remove the plasma fraction and to place the cells in an appropriate buffer or media for subsequent processing steps. In some non-limiting examples, the cells are washed with phosphate buffered saline (PBS). In an alternative examples, the wash solution lacks calcium and may lack magnesium or may lack many if not all divalent cations. Initial activation steps in the absence of calcium can lead to magnified activation. The washing step can be accomplished by methods known in the art, such as by using a semi-automated "flow-through" centrifuge (for example, the Cobe 2991 cell processor, the Baxter CYTOMATE®, or the HAEMONETICS CELL SAVER 5®) according to the manufacturer's instructions. After washing, the cells can be resuspended in a variety of biocompatible buffers, such as a saline solution with or without buffer. Alternatively, the undesirable components of the apheresis sample can be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, T cells can isolated by incubation with anti-CD3/anti-CD28 (e.g., 3×28)-conjugated beads, such as DYNABEADS™ M-450 CD3/CD28 T, for a time period sufficient for positive selection of the desired T cells, see U.S. Publication Application No. 20140271635 A1. In a non-limiting example the time period is about 30 minutes. In other non-limiting examples, the time period ranges from 30 minutes to 36 hours or longer and all integer values there between. In further non-limiting examples, the time period is at least 1, 2, 3, 4, 5, 6 hours, 10 to 24 hours, 24 hours or longer. Longer incubation times can be used to isolate T cells in any situation where there are few T cells as compared to other cell types, such in isolation from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. Multiple rounds of selection can also be used.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20 CD11b, CD16, HLA-DR, and CD8. A T cell population can be selected that expresses one or more cytokines. Methods for screening for cell expression are disclosed in PCT Publication No. WO 2013/126712.

For isolation of a desired population of cells by positive or negative selection, the concentration of cells and surface (e.g., particles such as beads) can be varied. Into ensure maximum contact of cells and beads. In some embodiments, a concentration of 1 billion cells/ml is used. In further embodiments, greater than 100 million cells/rill is used. In other embodiments, a concentration of cells of 10, 15, 20, 25, 30, 350 40, 45, 50, 65, 70, 75, 80, 85, 90, 95, or 100 million cells/nil is used. Without being bound by theory, using high concentrations can result in increased cell yield, cell activation, and cell expansion. Lower concentrations of cells can also be used. Without being bound by theory, significantly diluting the mixture of T cells and surface (e.g., particles such as beads), interactions between e particles and cells is minimized. This selects for cells that express h amounts of desired antigens to be bound to the particles. For example, CD4+ T cells express higher levels of CD28 and are more efficiently captured than CD8+ T cells in dilute concentrations. In some embodiments, the concentration of cells used is $5 \times 10^6$/ml. In other embodiments, the concentration used can be from about $1 \times 10^5$/ml to $1 \times 10^6$/ml, and any integer value in between.

Cells can be incubated on a rotator for varying lengths of time at varying speeds at either 2-10° C. or at room temperature. T cells for stimulation can also be frozen after a washing step. Without being bound by theory, the freeze and subsequent thaw step provides a more uniform product by removing granulocytes and to some extent monocytes in the cell population. After the washing step that removes plasma and platelets, the cells can be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Elespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen, see U.S. Publication No. 2014-0271635 A1.

Blood samples or apheresis product can be collected from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one aspect a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. In certain aspects, cryopreserved cells are thawed and washed as described herein and allowed to rest for one hour at room temperature prior to use. Blood samples or apheresis product can be collected from a subject when needed, and not frozen.

T cells can be activated and expanded generally using methods as described, for example, in U.S. Pat. Nos. 6,352, 694; 6,534,055; 6,905,680; 6,692,964; 5,858,358; 6,887, 466; 6,905,681; 7,144,575; 7,067,318; 7,172,869; 7,232, 566; 7,175,843; 5,883,223; 6,905,874; 6,797,514; 6,867, 041; and U.S. Publication No. 20060121005.

T cells can be expanded by contact with a surface having attached thereto an agent that stimulates a CD3/TCR complex associated signal and a ligand that stimulates a costimulatory molecule on the surface of the T cells. In some non-limiting examples, T cell populations may be stimulated as described herein, such as by contact with an anti-CD3 antibody, or antigen-binding fragment thereof, or an anti-CD2 antibody immobilized on a surface, or by contact with a protein kinase C activator (e.g bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD28 antibody include 9,3, B-T3, XR-CD28 (Diaclone, Besancon, France) can be used as can other methods commonly known in the art (Berg et al., Transplant Proc. 30(8):3975-3977, 1998; Haanen et al., J. Exp. Med, 190(9): 13191328, 1999; Garland e: al., J. Immunol. Meth. 227(1-2):53-63, 1999).

Once the CAR is constructed, various assays can be used to evaluate the activity of the molecule, such as but not limited to, the ability to expand T cells following antigen stimulation, sustain T cell expansion in the absence of re-stimulation, and anti-cancer activities in appropriate in vitro and animal models.

Isolated immune cells expressing a CAR, such as T cells, for example CD3+ T cells such as CD4+ and/or CD8+ T cells, and/or NK cells, can be administered in a pharmaceutically acceptable carrier, such as buffered saline or another medium suitable for administration to a subject. The cells can be administered in conjunction with other cells, or in the absence of other cells. In one embodiment, compositions containing isolated populations of cells can also contain one or more additional pharmaceutical agents, such as one or more anti-microbial agents (for example, antibiotics, anti-viral agents and anti-fungal agents), anti-tumor agents (for example, fluorouracil, methotrexate, paclitaxel, fludarabine, etoposide, doxorubicin, or vincristine), depleting agents (for example, fludarabine, etoposide, doxorubicin, or vincristine), or non-steroidal anti-inflammatory agents such as acetylsalicylic acid, ibuprofen or naproxen sodium), cytokines (for example, interleukin-2), or a vaccine. Many chemotherapeutic agents are presently known in the art. In one embodiment, the chemotherapeutic agent is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

In other embodiments, a subject is administered the DNA encoding the CAR, to provide in vivo production. Immunization by nucleic acid constructs is well known in the art and taught, for example, in U.S. Pat. Nos. 5,643,578, and 5,593,972 and 5,817,637. U.S. Pat. No. 5,880,103 describes several methods of delivery of nucleic acids encoding to an organism. The methods include liposomal delivery of the nucleic acids. Such methods can be applied to the production of an antibody, or antibody binding fragments thereof, by one of ordinary skill in the art.

One approach to administration of nucleic acids is direct administration with plasmid DNA, such as with a mammalian expression plasmid. The nucleotide sequence encoding the disclosed antibody, or antibody binding fragments thereof, can be placed under the control of a promoter to increase expression.

In another approach to using nucleic acids, a disclosed CAR can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (Bacillus Calmette Guerin) provides another vector for expression of the disclosed antibodies (see Stover, Nature 351:456-460, 1991). In a specific non-limiting example, the vector is a lentiviral vector.

In one embodiment, a nucleic acid encoding a disclosed CAR, is introduced directly into cells. For example, the nucleic acid can be loaded onto gold microspheres by standard methods and introduced by a device such as Bio-Rad's HELIOS™ Gene Gun. The nucleic acids can be "naked," consisting of plasmids under control of a strong promoter. The nucleic acid can be RNA; RNA encoding the CAR can be directly administered to the cells. In some embodiments, the cells are NK cells or T cells.

In some embodiments the methods include administering to the subject a therapeutically effective amount of an antibody or aptamer that specifically binds a tumor associated antigen expressed by a tumor, in the subject wherein the antibody or aptamer is biotinylated. The method also includes administering to the subject the pharmaceutical composition of comprising a therapeutically effective amount of cells, such as CD3+ T cells and/or NK cells, expressing the CAR, or administering to the subject a therapeutically effective amount of a vector encoding the CAR, thereby treating the tumor.

Biotinylated aptamers or antibodies that specifically bind tumor associated antigens expressed by the tumor are administered to a subject prior to, or concurrent with, or after administration of the T cells or the vectors. The biotinylated antibodies or aptamers bind to target cells in the subject. The tumor associated antigen can be a tumor specific antigen. Exemplary antigens include antibodies and/or aptamers that specifically bind MUC-1, CD19 or CD20. Additional antibodies that can be biotinylated include cetuximab (anti-EGFR), nimotuzumab (anti-EGFR), panitumumab (anti-EGFR), retuximab (anti-CD20), omaliximab (anti-CD20), tositumomab (anti-CD20), trastuzumab (anti-Her2), gemtuzumab (anti-CD33), alemtuzumab (anti-CD52), and bevacuzimab (anti-VEGF). Thus, the disclosed methods can utilize biotin-conjugated cetuximab, biotin-conjugated retuximab, and biotin-conjugated HERCEPTIN® (trastuzumab). In some embodiments, the AT-CAR cells can be redirected to target and/or destroy vascular cells feeding the tumor, such as by using biotin conjugated bevcuzimab.

In some embodiments, a antibody is utilized that specifically binds a tumor associated antigen that is not biotinylated. For example, an unlabeled antibody or aptamer that binds to the tumor associated antigen can be used. In these embodiments, a second antibody that is biotinylated, and specifically binds the first antibody or aptamer, is also administered to the subject. Under such circumstances, the CAR will recognize and specifically bind the second antibody, which specifically binds the first antibody or aptamer.

Biotin can be conjugated to antibodies and aptamers using as chemical coupling and chemical cross-linkers. The biotinylated antibodies and/or biotinylated aptamers can be formulated for administered to a subject using techniques known to the skilled artisan. Formulations of the biotinylated antibodies and/or biotinylated aptamers can include pharmaceutically acceptable carriers and excipients. Agents included in the formulations will have different purposes depending, for example, on the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The administration of antibodies and aptamers to subject is known in the art.

A formulation of biotinylated antibodies and/or biotinylated aptamers can include one type of biotinylated molecule, or more than one, such as two, three, four, five, six or more types of biotinylated molecules that specifically bind tumor associated antigens. The formulation can include both biotinylated antibodies and biotinylated aptamers. The formulation can include biotinylated antibodies and/or biotinylated aptamers and that bind the same or different tumor associated antigens.

The biotinylated antibodies and/or biotinylated aptamers can be administered to a subject using techniques know of to those of skill in the art. Exemplary modes of administration include, but are not limited to, intravenous, intraperitoneal, and intratumoral injection. Other modes include, without limitation, intradermal, subcutaneous, intramuscular, intra-arterial, intramedullary, intracranial, intraspinal, and intrathecal (spinal fluids). Any known device useful for parenteral injection or infusion can be utilized.

Formulations comprising the biotinylated antibodies and/or biotinylated aptamers are administered to a subject in an amount which is effective for treating and/or prophylaxis of the specific indication or disease. In general, formulations comprising at least about 0.1 mg/kg to about 100 mg/kg body weight of a biotinylated antibody are administered to a subject. In some embodiments, the dosage is from about 1 mg/kg to about 10 mg/kg body weight of the tagged proteins daily, taking into account the routes of administration, symptoms, etc. The amount of biotinylated antibodies and/or biotinylated aptamers in formulations administered to a subject will vary between wide limits, depending upon the location, source, identity, extent and severity of the tumor, the age and condition of the individual to be treated, and other factors. A physician will ultimately determine appropriate dosages to be used.

Administration frequencies of the composition comprising CAR-expressing T cells, or the expression vector encoding the CAR and formulations of biotinylated antibodies and/or biotinylated aptamers will vary depending on factors that include the tumor being treated and the modes of administration. The compositions can be administered once, or can be administered multiple times. Each composition can be independently administered twice daily, every other day, every third day, every fourth day, every fifth day, every sixth day, once weekly, every eight days, every nine days, every ten days, bi-weekly, monthly and bi-monthly.

The duration of treatment will be based on the disease being treated and will be best determined by the attending physician. However, continuation of treatment is can be for days, weeks, months or years.

A composition including biotinylated antibodies and/or biotinylated aptamers can be administered to a subject before, after or concurrently with the population(s) of CAR-expressing T cells or the nucleic acid encoding the CAR. When more than one compositions including biotinylated antibodies and/or biotinylated aptamers are utilized, the administration can be staggered. In one non-limiting example, a first composition included biotinylated antibodies and/or biotinylated aptamers can be administered, followed by a second composition included biotinylated antibodies and/or biotinylated aptamers specific for a different tumor associated antigen, followed by a composition comprising CAR-expressing T cells. In another non-limiting example, a first composition included biotinylated antibodies and/or biotinylated aptamers can be administered, followed by a first composition comprising CAR-expressing T cells, followed by a second composition included biotinylated antibodies and/or biotinylated aptamers specific for a different tumor associated antigen, followed by a second composition comprising CAR-expressing T cells. In a third non-limiting example, a first composition included unlabeled antibodies and/or unlabeled aptamers can be administered, followed by a second composition included biotinylated antibodies specific for the unlabeled antibodies and/or unlabeled aptamers, respectively, followed by a composition comprising CAR-expressing T cells.

The subject receiving treatment can be a human or non-human animal. In some embodiments, the subject is a non-human primate, bird, horse, cow, goat, sheep, a companion animal, such as a dog, cat or rodent, or other mammal. In other embodiments, the subject is a human.

Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In some embodiments, the tumor is a lymphoid tumor. In other embodiments, the subject can also have a solid tumor, such as, but not limited to, breast cancer, ovarian cancer, gastric cancer or esophageal cancer.

For the treatment of a tumor, the method can also include administering to the subject a therapeutically effective amount of an additional chemotherapeutic agent, surgery or radiation. The chemotherapeutic agent can be an antibody. Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. The antibody can specifically bind programmed death (PD)-1 or programmed death ligand (PD-L1) (see below). Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

In further embodiments for the treatment of malignancies, a CAR-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation, peptide vaccine, such as that described in fzumoto et al. 2008 J Neurosurg 108:963-971. Exemplary chemotherapeutic agents include an anthracycline (e.g., doxorubicin (e.g., liposomal doxorubicin)), a vinca alkaloid (e.g., vinblastine, vincristine, vindesine, vinorelbine), an alkylating agent (e.g., cyclophosphamide, decarbazine, melphalan, Ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

General chemotherapeutic agents considered for use in combination therapies include anastrozole ARIMIDEX®), bicalutamide (CASODEX®), bleomycin sulfate (BLENOXANE®), busulfan (MYLERAN®), busulfan injection (BUSULFEX®), capecitabine (XELODA®), N4-pentoxycarbonyl-5-deoxy-5-fluorocytidine, carboplatin (PARAPLATIN®), carmustine (BICNU®), chlorambucil (LEUKERAN®), cisplatin (PLATINOL®), cladribine (LEUSTATIN®), cyclophosphamide (CYTOXAN® or NEOSAR®), cytarabine, cytosine arabinoside (CYTOSAR-U®), cytarabine liposome injection (DEPOCYT®), dacarbazine (DTIC-DOME®), dactinomycin (Actinomycin D, Cosmegan), daunorubicin hydrochloride (CERUBIDINE®), daunorubicin citrate liposome injection (DAUNOXOME®), dexamethasone, docetaxel (TAXOTERE®), doxorubicin hydrochloride (ADRIAMYCIN®, RUBEX®), etoposide (VEPESID®), fludarabine phosphate (FLUDARA®), 5-fluorouracil (ADRUCIL®, EFUDEX®), flutamide (EULEXIN®), tezacitibine, Gemcitabine (difluorodeoxycitidine), hydroxyurea (HYDREA®), Idarubicin (IDAMYCIN®), ifosfamide (IFEX®), irinotecan (CAMPTOSAR®), L-asparaginase (ELSPAR®), leucovorin calcium, melphalan (ALKERAN®), 6-mercaptopurine (PURINETHOL®), methotrexate (FOLEX®), mitoxantrone (NOVANTRONE®), mylotarg, paclitaxel (TAXOL®), phoenix (Yttrium90/MX-DTPA), pentostatin, polifeprosan 20 with carmustine implant (GLIADEL®), tamoxifen citrate (NOLVADEX®), teniposide (VUMON®), 6-thioguanine, thiotepa, tirapazamine (TIRAZONE®), topotecan hydrochloride for injection (HYCAMPTIN®), vinblastine (VELBAN®), vincristine (ONCOVIN®), and vinorelbine (NAVELBINE®). Exemplary alkylating agents include, without limitation, nitrogen mustards, ethylenimine derivatives, alkyl sulfonates, nitrosoureas and triazenes): uracil mustard (AMINOURACIL MUSTARD®, CHLORETHAMINACIL®, DEMETRYLDOPAN®, DESMETHYLDOPAN®, HAEMANTHAMINE®, NORDOPAN®, URACIL NITROGEN MUSTARD®, URACILLOST®, URACILMOSTAZA®, URAMUSTIN®, URAMUSTINE®), chlormethine (MUSTARGEN®), cyclophosphamide (CYTOXAN®, NEOSAR®, CLAFEN®, ENDOXAN®, PROCYTOX®, REVIMMUNE™), ifosfamide (MITOXANA®), melphalan (ALKERAN®), Chlorambucil (LEUKERAN®), pipobroman (AMEDEL®, VERCYTE®), triethylenemelamine (HEMEL®, HEXYLEN®, HEXASTAT®), triethylenethiophosphoramine, Temozolomide (TEMODAR®), thiotepa (THIOPLEX®), busulfan (BUSILVEX®, MYLERAN®), carmustine (BiCNU®), lomustine (CEENU®), streptozocin (ZANOSAR®), and Dacarbazine (DTIC-DOME®). Additional exemplary alkylating agents include, without limitation, Oxaliplatin (ELOXATIN®); Temozolomide (TEMODAR® and TEMODAL®); Dactinomycin (also known as actinomycin-D, COSMEGEN®); Melphalan (also known as L-PAM, L-sarcolysin, and phenylalanine mustard, ALKERAN®); Altretamine (also known as hexamethylmelamine (HMM), HEXYLEN®); Carmustine (BICNU®); Bendamustine (TREANDA®); Busulfan (BUSULFEX® and MYLERAN®); Carboplatin (PARAPLATIN®); Lomustine (also known as CCNU, CEENU®); Cisplatin (also known as CDDP, PLATINOL® and PLATINOL®-AQ); Chlorambucil (LEUKERAN®); Cyclophosphamide (CYTOXAN® and NEOSAR®); Dacarbazine (also known as DTIC, DIC and imidazole carboxamide, DTIC-DOME®); Altretamine (also known as hexamethylmelamine (HMM), HEXYLEN®); Ifosfamide (IFEX®); Prednumustine; Procarbazine (MATULANE®); Mechlorethamine (also known as nitrogen mustard, mustine and mechloroethamine hydrochloride, MUSTARGEN®); Streptozocin (ZANOSAR®); Thiotepa (also known as thiophosphoamide, TESPA and TSPA, THIOPLEX®); Cyclophosphamide (ENDOXAN®, CYTOXAN®, NEOSAR®, PROCYTOX®, REVIMMUNE®); and Bendamustine HCl (TREANDA®). Exemplary mTOR inhibitors include, e.g., temsirolimus; ridaforolimus (formally known as deferolimus, (1R,2R,4S)-4-[(2R)-2[(1R,9S,12S,15R,16E,18R,19R,21R,23S,24E,26E,28Z,30S,32S,35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383); everolimus (AFINITOR® or RAD001); rapamycin (AY22989, SIROLIMUST®); sim.apimod (CAS164301-51-3); emsirolimus, (5-{2,4-Bis [(3S)-3-methylmorpholin-4-yl]pyrido[2,3-d]pyrimidin-7-yl}-2-methoxyphenyl)methanol. (AZD8055); 2-Amino-8-[trans-4-(2-hydroxyethoxy)cyclohexyl]-6-(6-methoxy-3-pyridinyl)-4-methyl-pyrido[2,3-d]pyrimidin-7(8H)-one (PF04691502, CAS 1013101-36-4); and N$^2$[1,4-dioxo-4-[[4-(4-oxo-8-phenyl-4H-1-benzopyran-2-yl)morpholinium-4-yl]methoxy]butyl]-L-arginylglycyl-L-α-aspartylL-serine-, inner salt (SF1126, CAS 936487-67-1), and X1,765. Exemplary immunomodulators include, e.g., afutuzumab (available from ROCHE®); pegfilgrastim (NEULASTA®); lenalidomide (CC-5013, REVLIMID®); thalidomide (THALOMID®), actimid (CC4047); and IRX-2 (mixture of human cytokines including interleukin 1, interleukin 2, and interferon γ, CAS 951209-71-5, available from IRX Therapeutics). Exemplary anthracyclines include, e.g., doxorubicin (Adriamycin® and RUBEX®); bleomycin (LENOXANE®); daunorubicin (dauorubicin hydrochloride, daunomycin, rubidomycin hydrochloride, CERUBIDINE®); daunorubicin liposomal (daunorubicin citrate liposome, DAUNOXOME®); mitoxantrone (DHAD, NOVANTRONE®); epirubicin (ELLENCE™); idarubicin (IDAMYCIN®, IDAMYCIN PFS®): mitomycin C (MUTAMYCIN®); geldanamycin; herbimycin; ravidomycin; and desacetylravidomycin. Exemplary vinca alkaloids include, e.g., vinorelbine tartrate (NAVELBINE®), Vincristine (ONCOVIN®), and Vindesine (ELDISINE®)); vinblastine (also known as vinblastine sulfate, vincaleukobiastine and VLB, ALKABAN-AQ® and VELBAN®); and vinorelbine (NAVELBINE®). Exemplary proteosome inhibitors include bortezomib (VELCADE®); carfilzarnib (PX-171-007, (S)-4-Methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenythutanamido)-pentanamide); marizomib (NPI-0052); ixazomib citrate (MLN-9708); delanzomib (CEP-18770); and O-Methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide (ONX-0912). Exemplary GITR agonists include, e.g., GITR fusion proteins and anti-GITR antibodies (e.g., bivalent anti-GITR antibodies) such as, e.g., a GUM fusion protein described in U.S. Pat. No. 6,111,090, European Patent No.: 090505B1, U.S. Pat. No. 8,586,023, PCT Publication Nos.: WO 2010/003118 and 2011/090754, or an anti-GITR antibody described, e.g., in U.S. Pat. No. 7,025,962, European Patent No. 194718381, ˉU.S. Pat. Nos. 7,812,135, 8,388,967, 8,591, 886, European Patent No. EP 1866339, PCT Publication No. WO 2011/028683, PCT Publication No. WO 2013/039954, PCT Publication No. W02005/007190, PCT Publication No. WO 2007/133822, PCT Publication No. WO2005/055808, PCT Publication No. WO 1999/40196, PCT Publication No. WO 2001/03720, PCT Publication No. WO 1999/20758, PCT Publication No. WO2006/083289, PCT Publication No. WO 2005/115451, U.S. Pat. No. 7,618,632, and PCT Publication No. WO 2011/051726.

In some embodiments, the subject can be administered an agent which enhances the activity of a CAR-expressing cell. For example, in one embodiment, the agent can be an agent which inhibits an inhibitory molecule. Inhibitory molecules, e.g., Programmed Death 1 (PD-1), can, in some embodiments, decrease the ability of a CAR-expressing cell to mount an immune effector response. Examples of inhibitory molecules include PD-1, PD-L1, CTLA4, LAG3, VISTA, BILA, LAIR1, CD160, 294 and TGFR-beta. Inhibition of an inhibitory molecule, e.g., by inhibition at the DNA, RNA or protein level, can optimize a CAR-expressing cell performance. In embodiments, an inhibitory nucleic acid, e.g., an inhibitory nucleic acid, e.g., a dsRNA, e.g., a siRNA or shRNA, can be used to inhibit expression of an inhibitory molecule in the CAR-expressing cell. In an embodiment the inhibitor is a shRNA. In an embodiment, the inhibitory molecule is inhibited within a CAR-expressing cell. In these embodiments, a dsRNA molecule that inhibits expression of the inhibitory molecule is linked to the nucleic acid that encodes a component, e.g., all of the components, of the CAR. In one embodiment, the inhibitor of an inhibitory signal can be, e.g., an antibody or antibody fragment that binds to an inhibitory molecule. For example, the agent can be an antibody or antibody fragment that binds to PD-1, PD-L1, PD-L2 or CTLA4 (e.g., ipilimumab (also referred to as MDX-010 and MDX-101 and marketed as YERVOY®; Bristol-Myers Squibb; Tremelimumab (IgG2 monoclonal antibody available from Pfizer, formerly known as ticilimumab, CP-675,206).). In an embodiment, the agent is an antibody or antibody fragment that binds to TIM3. In an embodiment, the agent is an antibody or antibody fragment that binds to LAG3.

Programmed Death (PD)-1 is an inhibitory member of the CD28 family of receptors that also includes CD28, CTLA-4, ICOS, and BTLA. PD-1 is expressed on activated B cells, T cells and myeloid cells (Agata et al. 1996 Int. Immunol 8:765-75). Two ligands for PD-1, PD-L1 and PD-L2 have been shown to downregulate T cell activation upon binding to PD-1 (Freeman et al. 2000 J Exp Med 192:1027-34; Latchman et al. 2001 Nat humunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314: Konishi et al. 2004 Clin Cancer Res 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a CCR4 CAR described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and PCT Publication No. WO2006/121168. Pidilizumab (CT-011; Cure Tech) is a humanized IgG1k monoclonal antibody that binds to PD-1. Pidilizumab and other humanized anti-PD-1 monoclonal antibodies are disclosed in PCT Publication No. WO2009/101611. Lambrolizumab (also referred to as MK03475; Merck) is a humanized $IgG_4$ monoclonal antibody that binds to PD-1. Lambrolizumab and other humanized anti-PD-1 antibodies are disclosed in U.S. Pat. No. 8,354,509 and PCT Publication No. WO2009/114335. MDPL3280A (Genentech/Roche) is a human Fc optimized $IgG_1$ monoclonal antibody that binds to PD-L1. MDPL3280A and other human monoclonal antibodies to PD-L1 are disclosed in U.S. Pat. No. 7,943,743 and U.S. Publication No. 2012/0039906. Other anti-PD-L1 binding agents include YW243.55.S70 (heavy and light chain variable regions are shown in SEQ ID NOs: 20 and 21 in PCT Publication No. WO2010/077634) and MDX-1 105 (also referred to as BMS-936559, and, e.g., anti-PD-L1 binding agents disclosed in PCT Publication No. WO2007/005874). AMP-qqqqq4 (B7-DCIg; Amplimmune; e.g., disclosed in PCT Publication No. WO2010/027827 and PCT Publication No. WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, U.S. Publication No. 2010/028330, and/or U.S. Publication No. 2012/0114649.

Kits

Kits are also provided. For example, kits for treating a subject with a tumor. The kits will typically include a disclosed nucleic acid encoding a CAR, T cell expressing a CAR or compositions including such molecules. Optionally, the kit can also include a biotinylated antibody or aptamer that specifically binds a tumor associated antigen.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments, the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of the antibodies, antigen binding fragments, conjugates, nucleic acid molecules, or compositions included in the kit. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

A new CAR was generated with potent activity composed of the affinity-enhanced monomeric streptavidin (mSA2) protein, engineered to have high affinity for biotin compared to other monomeric and dimeric avidins ($K_d$=5.5×10$^{-9}$ at 37° C).[17] Higher-affinity can lead to greater T cell activation and antitumor response in the AT-CAR format (Ma et al., Proc Natl Acad Sci U S A 2016; 113:E450-80. It was determined that mSA2 CAR T cells are efficiently stimulated by plate-immobilized biotin and are capable of potent target cell lysis and cytokine production when combined with biotinylated TAA-specific antibodies.

Example 1

Materials and Methods

Lentiviral vector construction and virus production: The CAR coding regions listed in FIG. 6 were synthesized (Integrated DNA Technologies) and cloned into the pSICO-EF1 vector using Gibson Assembly (Lohmueller et al., Sci Rep 2016; 6:31740). Virus was generated using the above described transfer vectors following methods described previously in detail (Lohmueller et al., Sci Rep 2016; 6:31740).

Antibody biotinylation: Antibodies FMC63, Rituximab and Cetuximab were purchased (Absolute Antibody) and biotinylated using the EZ-Link NHS biotin kit (ThermoFisher Scientific) and were determined by HABA assay to contain an average of 3-4 molecules of biotin per antibody.

Cell line culture: Human tumor cell lines Jurkat Clone E6-1 (TIB-152), K562 (CCL-243), and Raji (CCL-86) were obtained from American Type Culture Collection (ATCC) and cultured at 37° C. in RPMI medium supplemented with 1×MEM amino acids solution, 10 mM Sodium Pyruvate, 10% fetal bovine serum (FBS) and Penicillin-Streptomycin (Life Technologies). K562+CD19 cells that stably express full-length CD19 were generated by transducing K562 cells with CD19-expressing lentivirus and sorting for cells positive for CD19 expression. HEK293T (human embryonic kidney) cells (ATCC) were cultured at 37° C. in DMEM supplemented with 10% FBS, and Penicillin-Streptomycin.

Primary human T cell culture and lentiviral transduction: All experiments were performed on PBMC isolated from de-identified human Buffy Coat samples purchased. Human T cells were cultured in supplemented RPMI media as described for cell lines above, however, 10% Human AB serum (Gemini Bio Products) was used instead of FBS, and the media was further supplemented with 100 U/ml human IL-2 IS and 1 ng/ml IL-15 (Miltenyi Biotec). PBMC were isolated from a Buffy Coat from healthy volunteer donors using Ficoll centrifugation and total human T cells were isolated using the Human Pan T cell isolation kit (Miltenyi Biotec). T cells were stimulated and expanded using Trans-Act Human T cell Activation Reagent (Miltenyi Biotec). For transduction, two days after addition of TransAct, lentivirus was added to cells at an MOI of 10-50 in the presence of 6 µg/ml of DEAE-dextran (Sigma Aldrich). After 18 hours, cells were washed and resuspended in fresh T cell media containing 100 U/ml IL-2 and 1 ng/ml IL-15. After an additional 12 days of stimulation and expansion, CAR+ cells were flow-sorted by TagBFP expression. To obtain sufficient numbers of cells for experiments, sorted CAR+ cells then underwent an additional TransAct stimulation cycle prior to being assayed.

Flow cytometry staining: Cells were stained using the indicated antibodies and diluted in flow cytometry buffer (PBS+2% FBS), for 30 minutes at 4° C. followed by two washes with flow cytometry buffer. Live cells were gated based on forward and side scatter and CAR+ cells were gated on TagBFP expression. 50,000 total events were recorded per sample.

Plate-immobilized biotin stimulation assay: High protein-binding 96 well flat-bottom plates (Corning) were coated with 10 µg/ml of biotinylated antibody in PBS or with PBS alone for 2 hours at 37° C. and washed 2 times with PBS. 100,000 CAR T cells were incubated on the plate for 18 hours. After incubation, cells were stained with antibodies against T cell activation markers CD69-PE (BD Biosciences), CD62L-FITC (BD Biosciences) and CD107a-APC (BD Biosciences) and evaluated for marker expression by flow cytometry.

CAR T cell and target cell antibody mediated activation co-incubation assay: 100,000 primary T cells were co-cultured with 10,000 target cells and the indicated amounts of biotinylated antibodies for 18 hours. After incubation, cells were stained with antibodies against T cell activation markers CD69-PE (BD Biosciences) and CD62L-FITC (BD Biosciences) and evaluated for activation marker expression by flow cytometry. Supernatants from these co-cultures were also collected and analyzed for the presence of IFNγ by ELISA (BioLegend). Assays were performed in triplicate and average IFNγ production was plotted with standard deviation.

Target cell lysis assay: Target cells were stained with CELLTRACE™ Yellow following manufacturer's recommendation (ThermoFisher), re-suspended in DMEM-media and plated at 10,000 cells per well in 50 µl in a 96 well V-bottom plate. 50 µL of CAR T cells were added at E:T ratio of 10:1 (100,000 target cells). Plates underwent a quick spin to collect cells at the bottom of the wells and were incubated at 37° C. for 18 hours. To identify lysed cells, samples were stained with GHOSTDYE™ Red Viability Dye (Tonbo Biosciences) and analyzed by flow cytometry. Target cells were identified by CELLTRACE™ Yellow and lysed target cells were identified by positive GHOSTDYE™ staining. Specific cytotoxicity was calculated by the equation: 100* (% experimental lysis−% target-only lysis)/(100−% target-only lysis).

Example 2

Results

Lentiviral vectors encoding two mSA2 CAR signaling domain variants, mSA2-4-1BB-CD3ζ and mSA2-CD28-CD3ζ (FIG. 1B) were constructed. Driven by the EF1α promoter, CAR-coding regions consisted of the murine Igκ leader sequence, the codon-optimized mSA2 protein domain, the CD8α-hinge spacer domain, the CD28 transmembrane domain, either the CD28 or the 4-1BB cytoplasmic domain and the CD3ζ cytoplasmic domain. Additionally, to mark transduced cells, the TagBFP marker gene was added via a T2A co-translation peptide (Lohmueller et al., Sci Rep 2016; 6:31740). An anti-CD19 CAR, FMC63-CD28ζ, which consisted of the FMC63 scFv, the IgG4 extracellular spacer, CD28 transmembrane and co-signaling domains and CD3ζ, was also constructed as a positive control CAR (Kochenderfer et al., J Immunother 2009; 32:689-702). All the vectors were packaged into lentiviruses and transduced into primary human T cells.

Figure 2A:
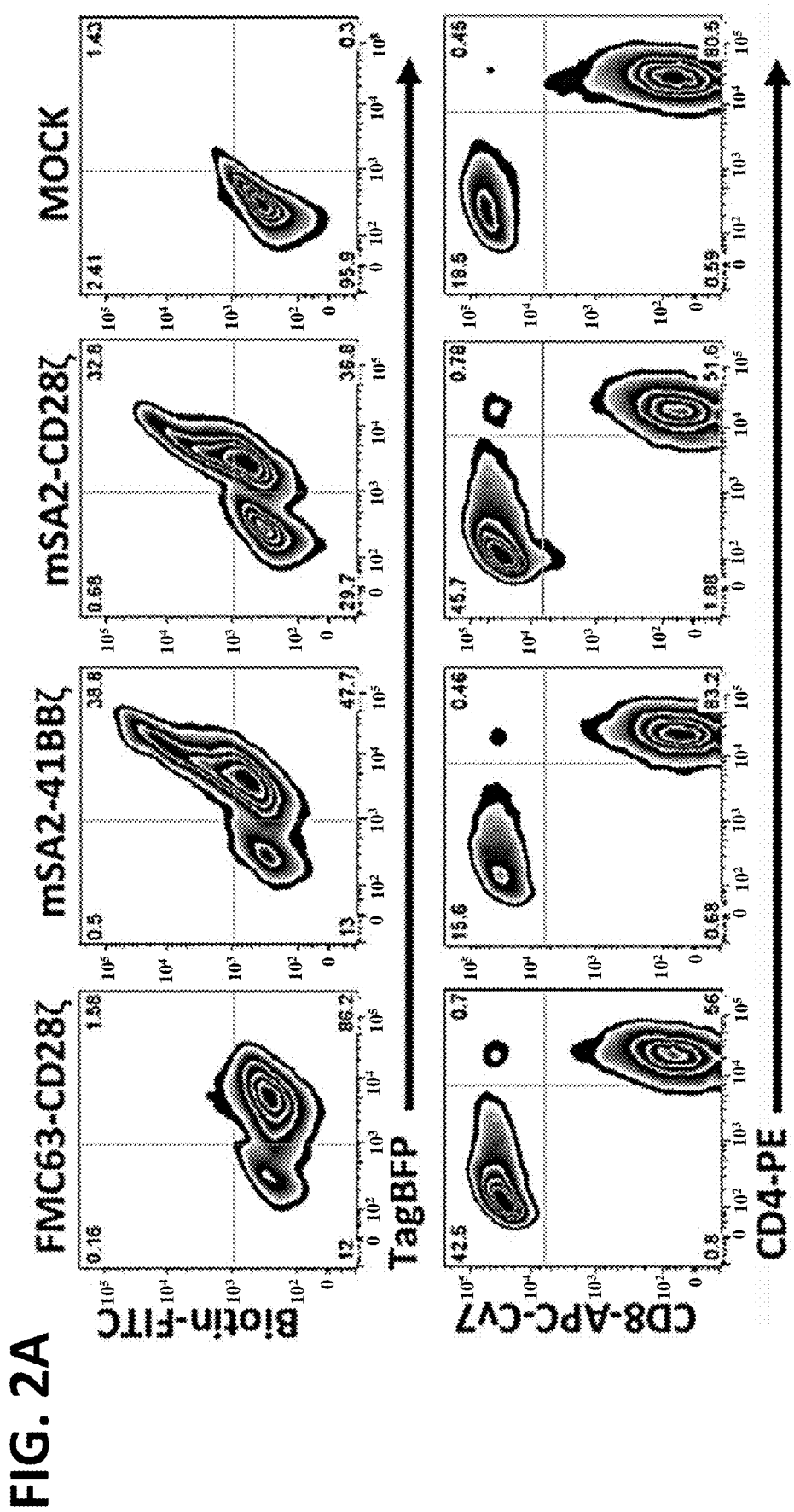
FIGS. 2A-2B. Cell surface expression of mSA2 CARs and activation of primary human T cells. (A) Primary human T cells were transduced with lentiviruses encoding the mSA2-41BBζ CAR, the mSA2-CD28ζ CAR or the FMC63-CD28ζ CAR. After one stimulation cycle, cells were sorted by flow cytometry for TagBFP expression and stained with biotin-FITC or for CD4 and CD8 expression. (B) CAR T cells were plated in the presence of the indicated plate-immobilized biotinylated antibody for 18 hours and assayed by flow cytometry for T cell activation markers CD69, CD107a, and CD62L (down-regulated upon activation).
Figure 2B:
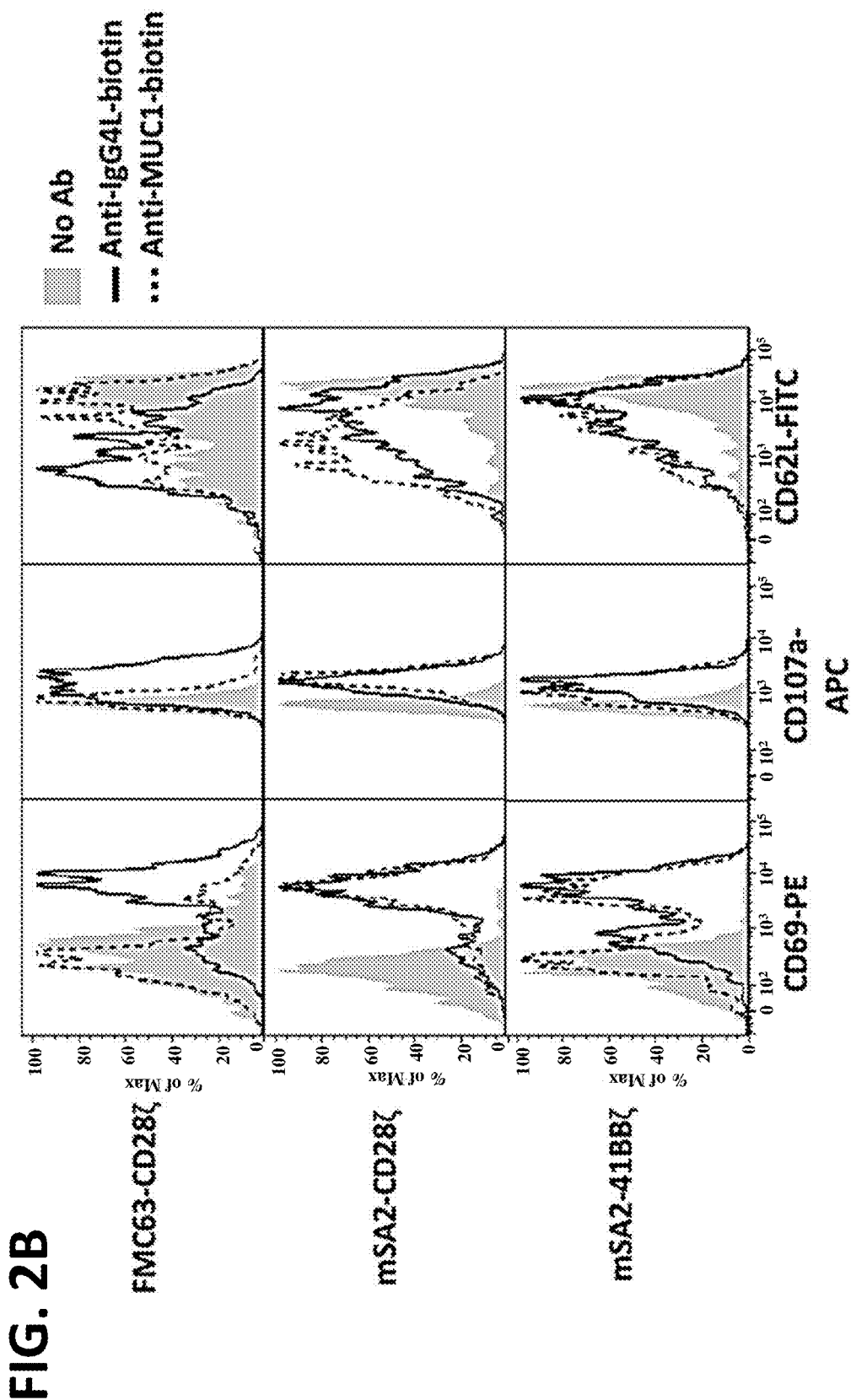

It was found that the mSA2 CARs were efficiently expressed on the cell surface (FIG. 2A) and that the mSA2 CAR T cells could be activated by plate-bound biotin (FIG. 2B). Following one stimulation cycle, transduced T cells were sorted for TagBFP expression and then stained with biotin-FITC. The staining with biotin-FITC was specific to mSA2 CAR T cells and correlated with TagBFP expression (FIG. 2A). T cells were also evaluated for helper and cytotoxic populations based on CD4 and CD8 expression. The mSA2 CAR T cells could be efficiently activated by plate-immobilized biotin (FIG. 2B). Specifically, CAR T cells or control cells were incubated on plates coated with biotinylated antibodies for 18 hours and then assayed cells for T cell activation markers by flow cytometry. Incubation with plate immobilized biotin led to the upregulation of T cell activation markers CD69 and CD107a as well as the downregulation of CD62L. It was found that FMC63-CD28ζ CAR T cells were activated by the plate immobilized anti-hIgG4 antibody that can bind to the IgG4 extracellular spacer but not by a biotinylated antibody against an irrelevant target (anti-MUC1 antibody H15K6).

Figure 3A:
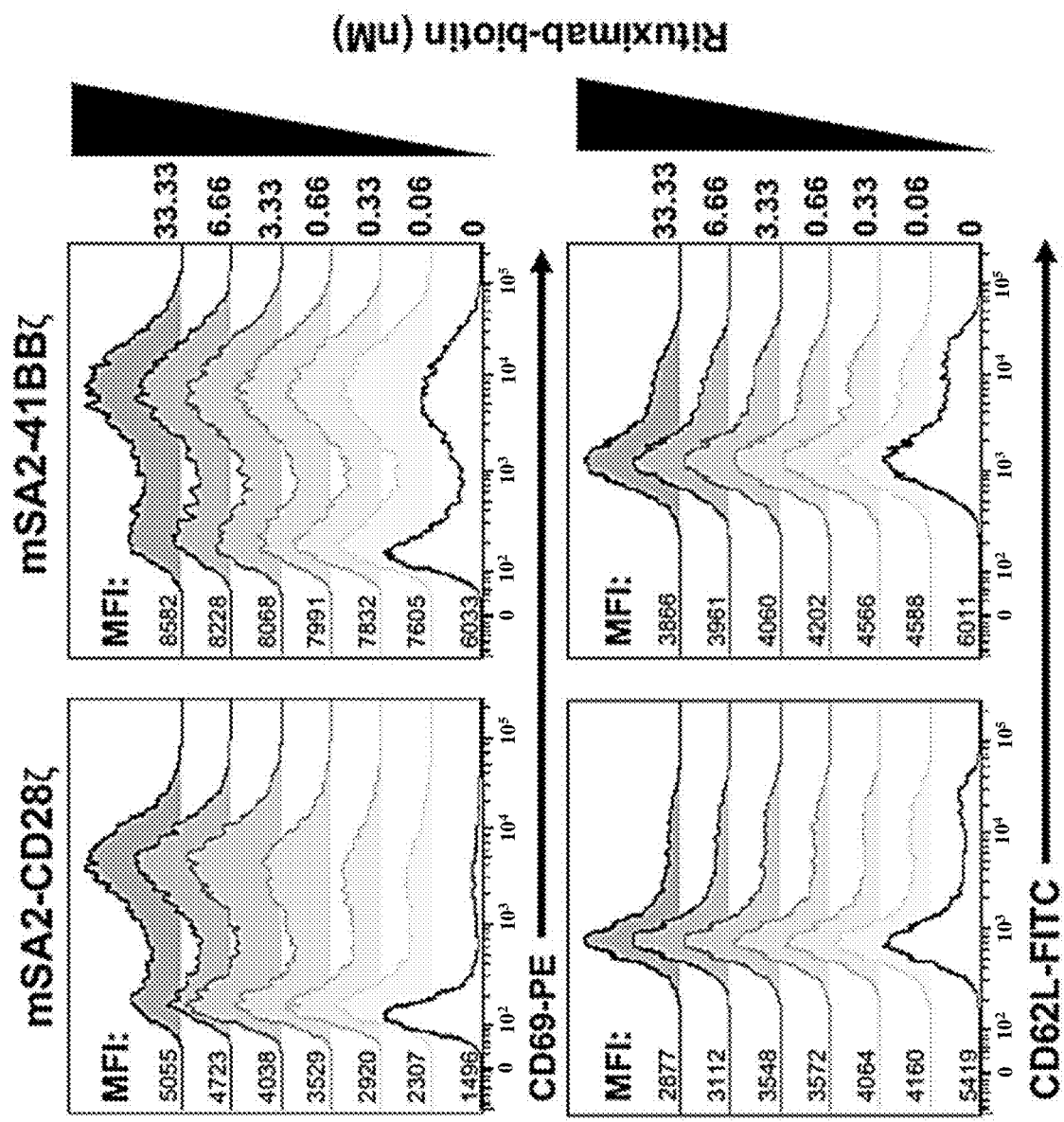
FIGS. 3A-3C. mSA2 CAR T cells display biotinylated antibody dose-responsive effector functions. mSA2-CD28ζ or mSA2-41BBζ cells were incubated at an E:T ratio of 10:1 with CD20+ Raji tumor targets in the presence of increasing concentrations of biotinylated anti-CD20 antibody Rituximab for 18 hours. (A) Cells were stained for activation markers CD69 (upper panels) and CD62L (lower panels) and evaluated by flow cytometry. (B) Supernatants from co-incubations were evaluated by ELISA for interferon (IFN)γ production. (C) Co-incubations were performed similar to (A) and (B) however target cells were labeled with CELLTRACE™ Yellow were further evaluated by flow cytometry for viability by staining with GHOSTDYE™ Red. For (B) and (C), multiple ANOVA comparisons were performed. As the data did not have homogeneity of variance (Levene's test), Tukey's honest significant difference (HSD) was used for post hoc analysis between antibody conditions. "*" denotes a significance of p<0.01 and "NS" stands for not significant. Error bars represent standard deviations for n=3 replicates.
Figure 3B:
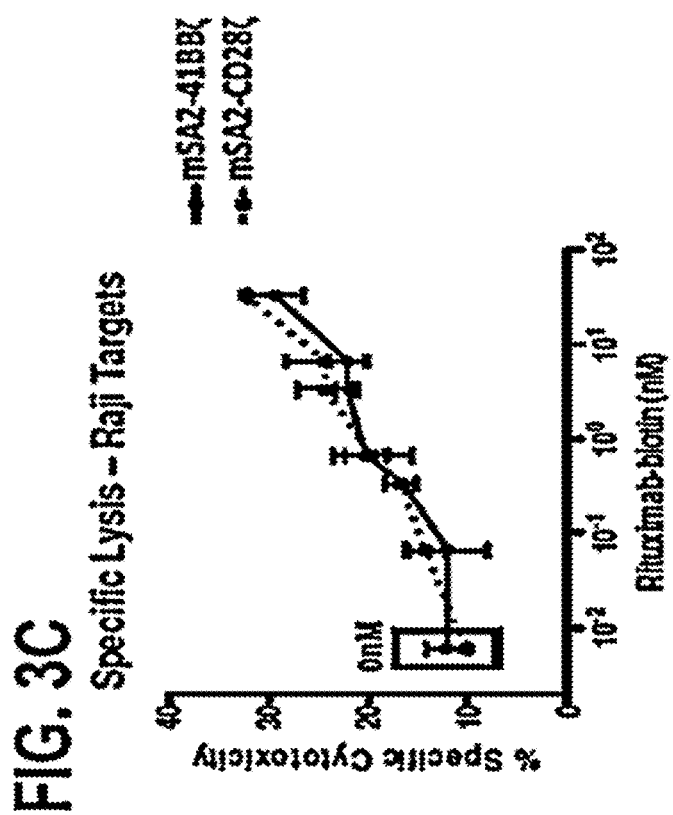
Figure 3C:
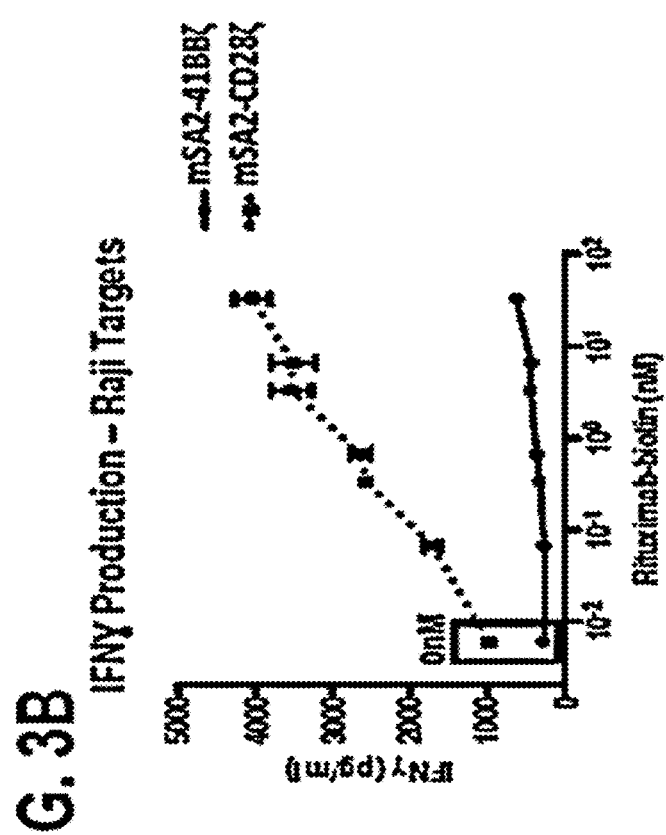
Figure 5:
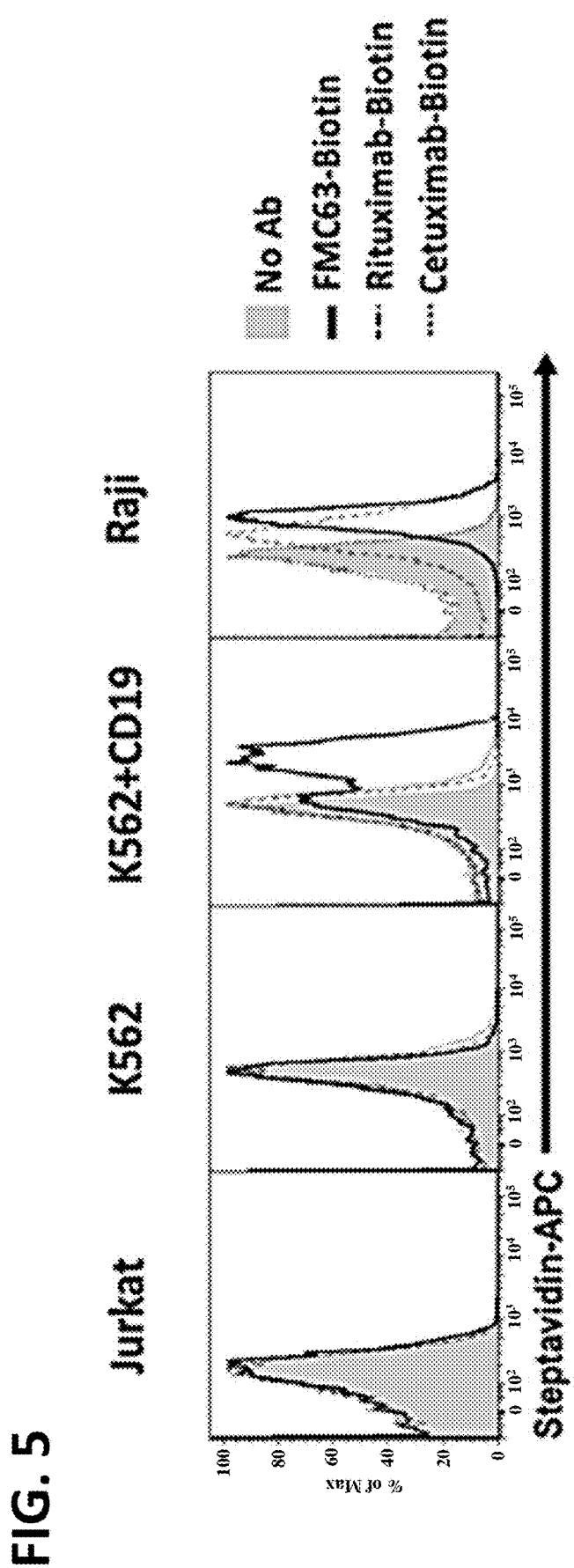
FIG. 5. Biotinylated antibody staining of target cell lines. Target cells (Jurkat, K562, K562+CD19 and Raji) were stained with the indicated biotinylated antibodies followed by staining with streptavidin conjugated to APC. Cells were then washed and analyzed by flow cytometry.
Figure 6A:
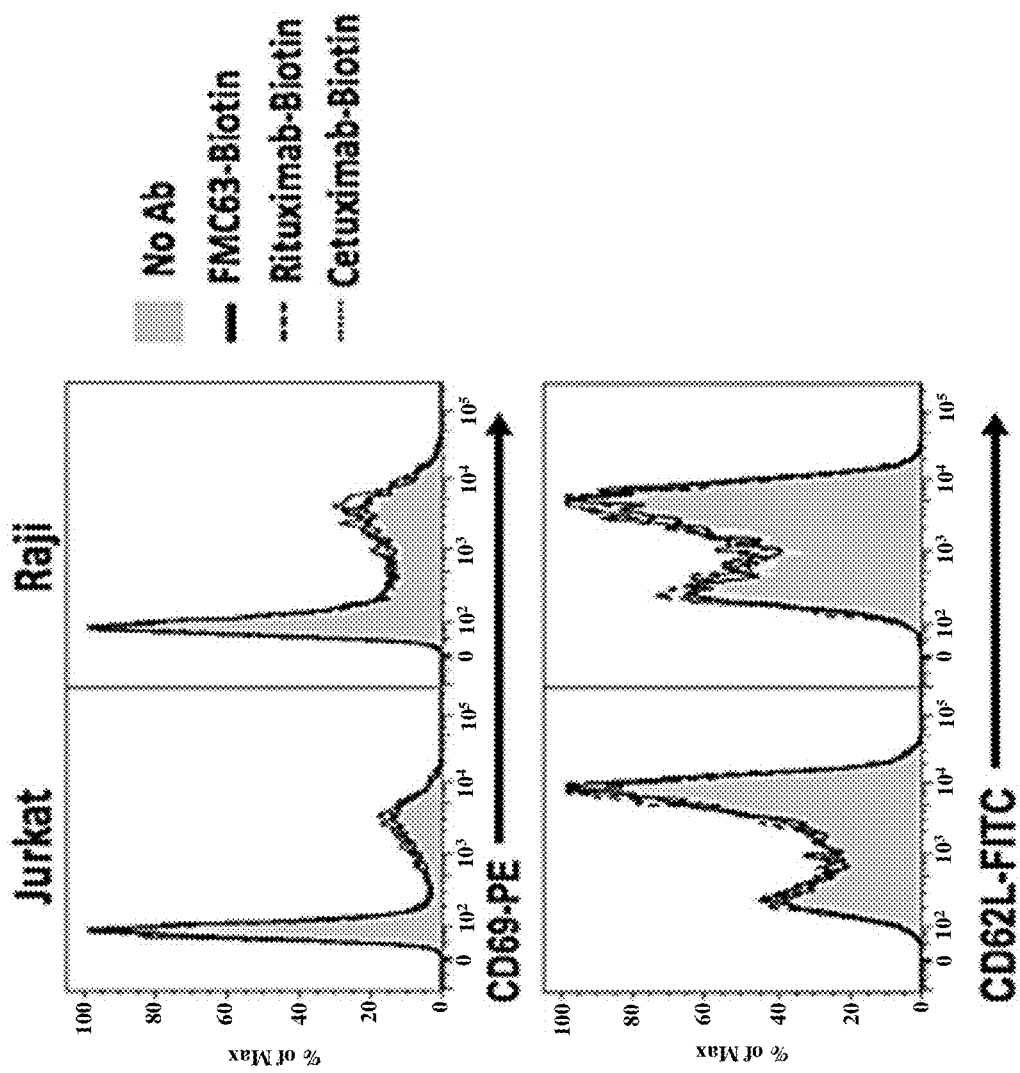
FIGS. 6A-6C. Lack of MOCK transduced T cell effector functions. (A) MOCK transduced T cells were incubated with Jurkat or Raji target cells for 18 hours at an effector to target (E:T) ratio of 10:1 in the presence of the indicated biotinylated antibodies at 5 μg/mL (33.33 nM). T cells were assayed by flow cytometry for expression of activation markers CD69 (top panels) and CD62L (lower panels). (B) Supernatants from co-incubations in (A) were isolated and evaluated by ELISA for IFNγ production. (C) MOCK transduced T cells and Raji Target cells were co-incubated for 18 hours at an E:T ratio of 10:1 in the presence of the indicated biotinylated antibodies at 5 μg/mL (33.33 nM) and evaluated for lysis. For (B) and (C), multiple ANOVA comparisons were performed. As the data did not have homogeneity of variance (Levene's test), Tukey's HSD was used for post hoc analysis between antibody conditions. "*" denotes a significance of p<0.01 and "NS" stands for not significant. Error bars represent standard deviations for n=3 replicates.
Figure 6C:
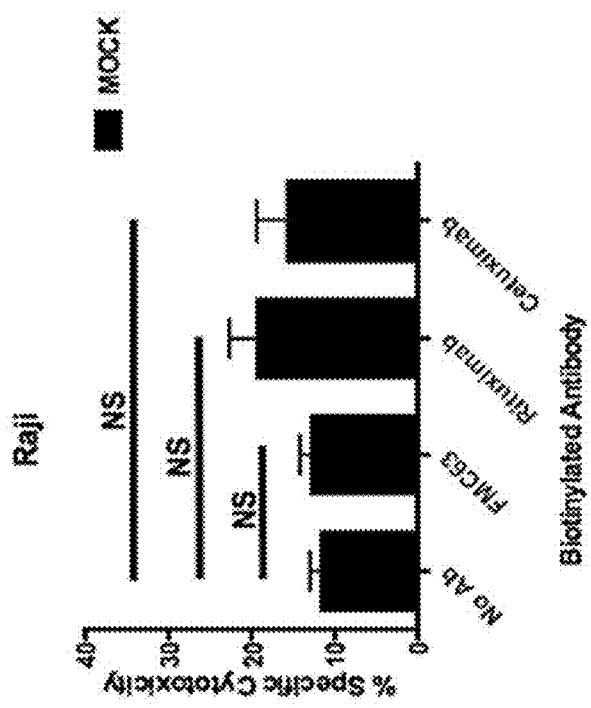
Figure 6B:
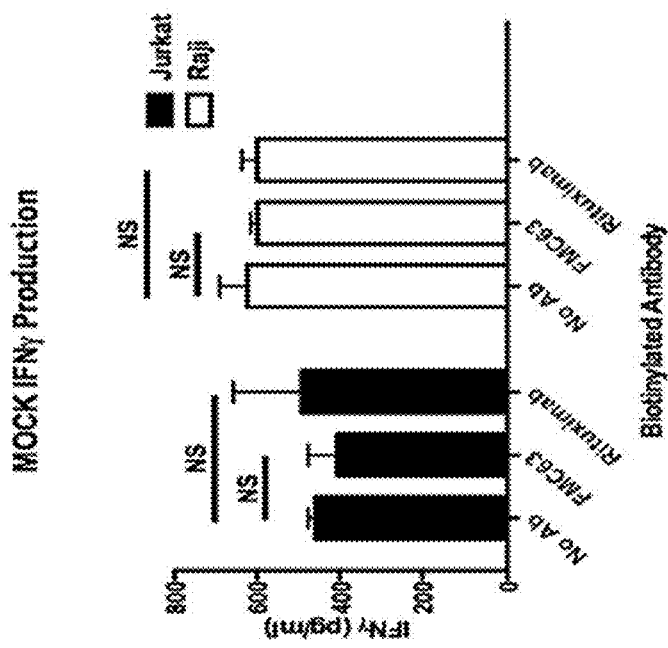

Next, it was tested if mSA2 CAR T cells could be combined with anti-tumor antibodies to mediate specific T cell effector functions. For these studies mSA2-41BBζ or mSA2-CD28ζ T cells were co-incubated with CD20+ Raji target cells (FIG. 5) in the presence of varying amounts of biotinylated Rituximab (anti-CD20). The mSA2 CAR T cells responded by up-regulating T cell activation markers in a dose-responsive manner to the biotinylated Rituximab (FIG. 3A). They also produced IFNγ (FIG. 3B) and performed target cell lysis (FIG. 3C) in a dose-responsive manner. mSA2-CD28ζ T cells produced vastly more IFNγ compared to the mSA2-41BBζ T cells, however, both showed comparable levels of specific target cell lysis. This result is consistent with previous findings for traditional CARs with CD28 versus 4-1BB co-signaling domains from several research groups (Brentjens et al., Clin Cancer Res 2007; 13:5426-35; Campana et al., Cancer J 2014; 20:134-40; Carpenito et al., Proc Natl Acad Sci U S A 2009; 106:3360-5.Finney et al., J Immunol 2004; 172:104-13). It is likely the result of established differences in CD28 and 4-1BB signaling pathways which signal via Akt and TRAFs, respectively (Brentjens et al., Clin Cancer Res 2007; 13:5426-35; Kane et al., Nat Immunol 2001; 2:37-44). Notably, incubating the mSA2 CAR T cells with biotinylated antibody and off-target cells lead neither to T cell activation nor any significant induction of T cell effector functions, indicating that immobilizing the antibodies on the surface of the target cells was necessary to initiate CAR T cell receptor signaling and that soluble antibody alone could not induce activation. As an additional control, it was found that MOCK transduced T cells, when combined with biotinylated antibodies, were not activated nor induced to produce cytokines or lyse tumor cells (FIG. 6).

Figure 4A:
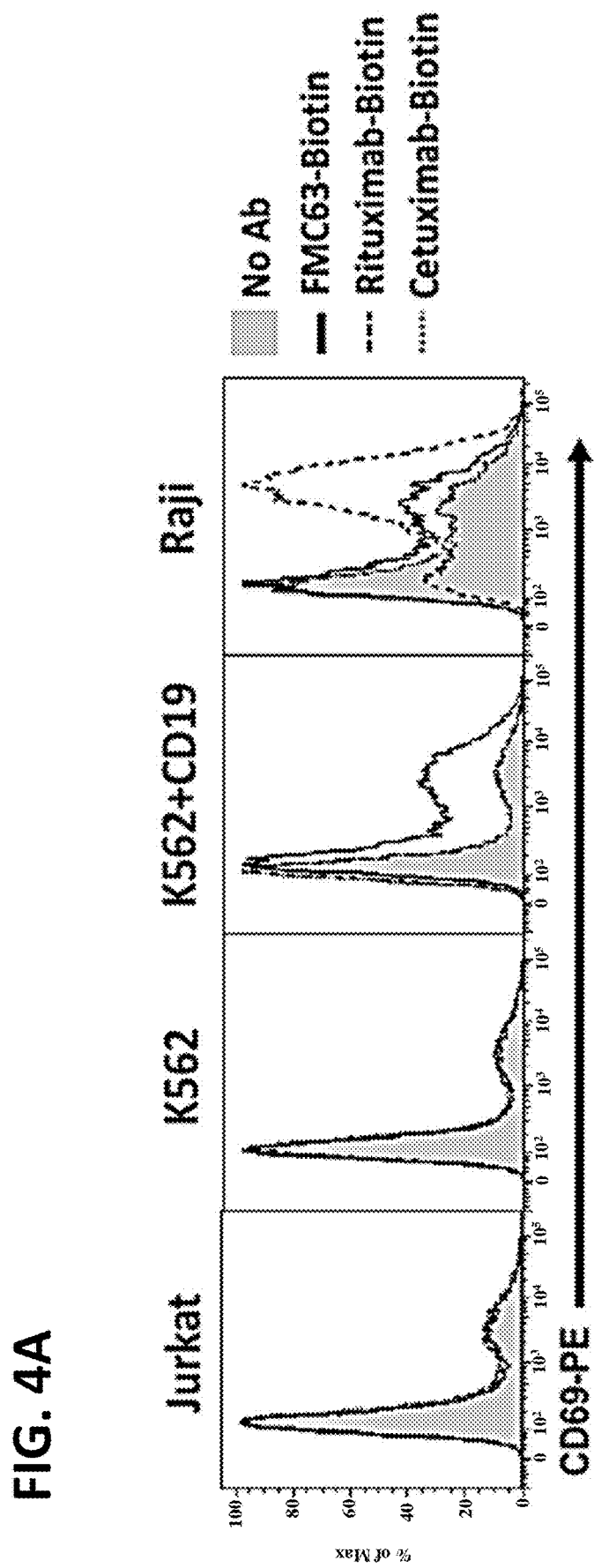
FIGS. 4A-4C. mSA2 CAR T cells display biotinylated-antibody mediated effector functions against various target cell lines. Tumor target cells, CAR T cells, and 5 μg/ml (33.33 nM) of the indicated antibodies were incubated for 18 hours and (A) cells were stained for the activation marker CD69 and evaluated by flow cytometry. (B) Supernatants from co-incubations were evaluated by ELISA for IFNγ production. (C) Co-incubations were performed similar to (A) and (B) however target cells were labeled with CELLTRACE™ Yellow were further evaluated by flow cytometry for viability by staining with GHOSTDYE™ Red. For (B) and (C), multiple ANOVA comparisons were performed. As the data did not have homogeneity of variance (Levene's test), Tukey's HSD was used for post-hoc analysis between antibody conditions. "*" denotes a significance of p<0.01 and "NS" stands for not significant. Error bars represent standard deviations for n=3 replicates.
Figure 4B:
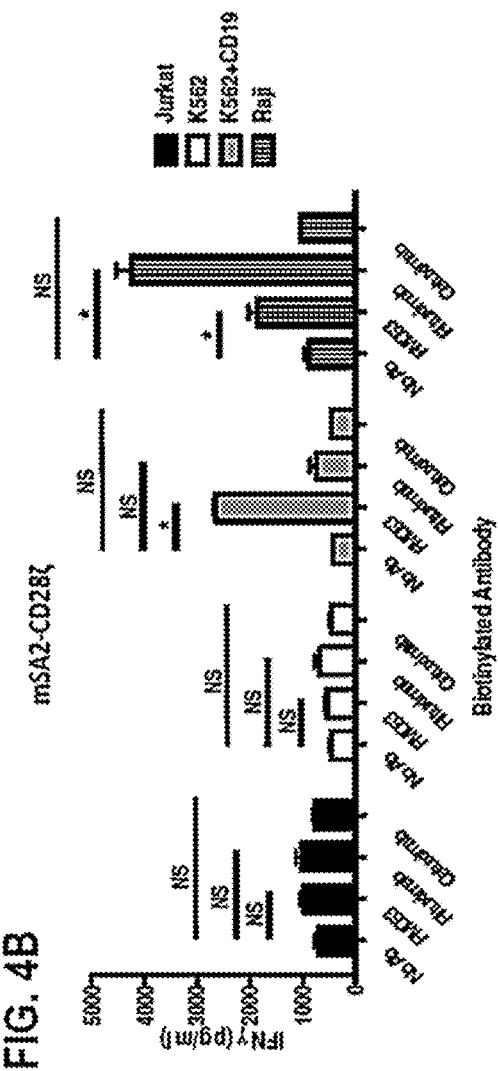
Figure 4C:
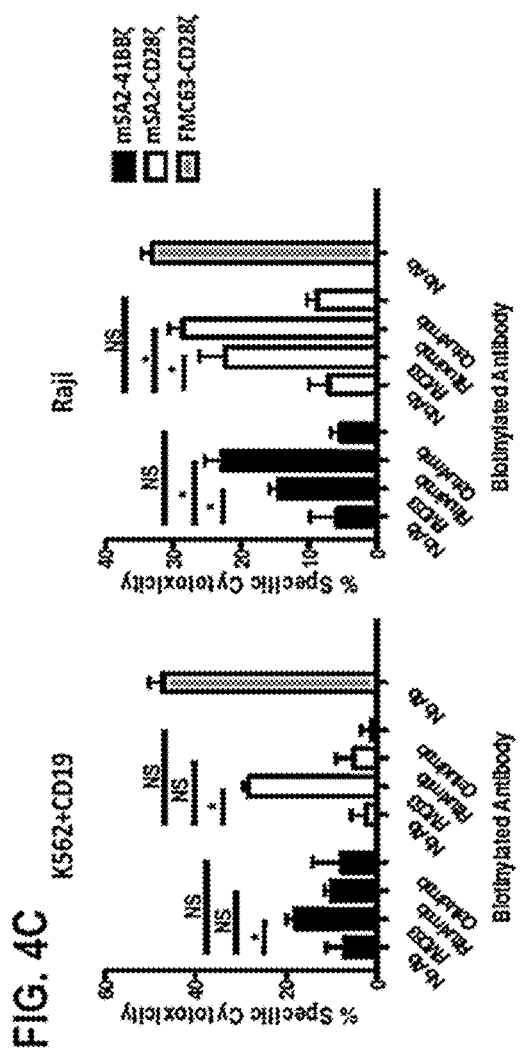

The activity of mSA2-41BBζ and mSA2-CD28ζ CAR T cells was tested, when combined with various antigen-positive and antigen-negative target cell lines, in the presence of biotinylated Rituximab, FMC63 (anti-CD19), or biotinylated Cetuximab (anti-EGFR) antibodies. Biotinylated Cetuximab served as a negative control as its target antigen, EGFR, is not expressed on any of the targeted cell lines. Target cell lines included Jurkat cells which are negative for both CD19 and CD20, K562 cells which are negative for both CD19 and CD20, K562 cells which are engineered to express CD19 (K562+CD19), and Raji cells which are naturally positive for both CD19 and CD20 (FIG. 5). Following co-incubation of T cells and target cells with the different biotinylated antibodies, it was found that the mSA2-CAR T cells were induced to express activation markers (FIG. 4A), produce IFNγ (FIG. 4B) and lyse target cells (FIG. 4C). Importantly, the presence of both the biotinylated antibody and the targeted antigen on the cancer cells was required for mSA2 CAR cells to be activated and functional. It was found that the lytic abilities of mSA2-CD28ζ CAR cells were comparable to the FMC63-CD28ζ positive control CAR.

In vivo testing of mSA2-41BBζ and mSA2-CD28ζ CAR T cells is tested in mice bearing human tumor xenografts with different biotinylated antibody doses and schedules. The potency of the biotinylated antibodies and mSA2 CAR T cells can be augmented by performing site-specific biotinylation on the antibodies at various amino acid positions and selecting for sites that give the most potent lysis, likely optimizing the formation of the T cell synapse (Ma et al., Proc Natl Acad Sci U S A 2016; 113:E450-8).

While it is known that tetrameric avidin can elicit antibody and cellular responses, additional studies are conducted determine immunogenicity of the monomeric mSA2 (Weir et al., Cancer Immunol Res 2014; 2:469-79). The monomeric form with fewer repeating structures elicits a more diminished antibody response. Nevertheless, mutations have been reported that can make tetrameric avidin less immunogenic, which are applied to the mSA2 protein domain (Yumura et al., Protein Sci 2013; 22:213-21). As many CARs in the clinic have immunogenic mouse antibody domains including the most common CAR FMC63, there could be a similar therapeutic window in which the mSA2-CAR T cells could function before being rejected. In comparison to other tag-CARs, the biotin tag can be better tolerated than PNE or FITC, which are entirely foreign molecules.

The mSA2-CAR is a new AT-CAR with potential for targeting several different antigens by T cells engineered to express a single CAR. Complementary to previously developed tag-CARs, the mSA2 avidin binding domain has a unique compact structure (122 amino acids in length) that make it suitable to targeting new antigens. This CAR can be used in combination with the ever-increasing list of FDA-approved tumor-targeting antibodies and antibodies in clinical development (Lohmueller and Finn, Pharmacol Ther 178: 31-47, 2017, incorporated herein by reference). It can also be combined with antibodies that display tumor-specificity but lack anti-tumor therapeutic activities on their own. In addition, the msa2-CAR can already be used as an off-the-shelf reagent for preselecting in vitro the best candidate antibodies for antigen binding domains of traditional CARs before proceeding with their construction.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method for treating a subject with a tumor, comprising administering to the subject a therapeutically effective amount of a monoclonal antibody that specifically binds a tumor associated antigen expressed by the tumor, wherein the monoclonal antibody is biotinylated, and administering to the subject a pharmaceutical composition, thereby treating the tumor in the subject, wherein the pharmaceutical composition comprises i) an effective amount of an expression vector comprising a promoter operably linked to a nucleic acid molecule encoding a chimeric antigen receptor comprising amino acids 1-369 of SEQ ID NO: 11 or amino acids 1-371 of SEQ ID NO: 12 or ii) an effective amount of CD3+T cells and/or natural killer cells transduced with the expression vector of (i), and a pharmaceutically acceptable carrier, thereby treating the tumor in the subject.

2. The method of claim 1, wherein the pharmaceutical composition comprises the CD3+T cells, and wherein the T cells are autologous to the subject.

3. The method of claim 1, wherein
a) the pharmaceutical composition comprises the CD3+ T cells, wherein the CD3+ T cells are CD3$^+$CD4$^+$ T cells and/or CD3$^+$CD8$^+$ T cells; and/or
b) the tumor associated antigen is MUC-1, CD19 or CD20.

4. The method of claim 1, wherein the subject is human.

5. The method of claim 1, wherein a) the tumor is a lymphoma or leukemia; or b) the tumor is a solid tumor.

6. The method of claim 1, wherein the chimeric antigen receptor comprises amino acids 1-371 of SEQ ID NO: 12.

7. The method of claim 1, wherein the expression vector comprises the nucleic acid sequence of SEQ ID NO: 13.

8. The method of claim 1, wherein the expression vector comprises the nucleic acid sequence of SEQ ID NO: 14.

9. The method of claim 1, wherein the expression vector comprises (a) the nucleic acid sequence of SEQ ID NO: 15; and/or (b) the nucleic acid of SEQ ID NO: 16.

10. The method of claim 1, wherein the expression vector comprises the nucleic acid sequence of SEQ ID NO: 17 or SEQ ID NO: 18.

11. The method of claim 1, wherein the expression vector comprises the nucleic acid sequence of SEQ ID NO: 19.

12. The method of claim 1, wherein the expression vector is codon-optimized for expression in human cells.

13. The method of claim 1, wherein the expression vector comprises the nucleic acid sequence of SEQ ID NO: 20 or SEQ ID NO: 21.

14. The method of claim 1, wherein the expression vector is a viral vector.

15. The method of claim 14, wherein the viral vector is a lentiviral vector or a gamma retroviral vector.

16. The method of claim 1, wherein the tumor associated antigen is EGFR or HER2.

17. A method for treating a subject with a tumor, comprising
transducing CD3+ T cells and/or natural killer cells from the subject with an expression vector comprising a promoter operably linked to a nucleic acid molecule encoding a chimeric antigen receptor comprising amino acids 1-369 of SEQ ID NO: 11 or amino acids 1-371 of SEQ ID NO: 12 to produce autologous transduced cells that express the chimeric antigen receptor:
administering to the subject a therapeutically effective amount of a monoclonal antibody that specifically binds a tumor associated antigen expressed by the tumor, wherein the monoclonal antibody is biotinylated; and
administering to the subject a therapeutically effective amount of the autologous transduced cells that express the chimeric antigen receptor, thereby treating the tumor in the subject.

18. The method of claim 17, wherein the tumor associated antigen is MUC-1, CD19 or CD20.

19. The method of claim 17, wherein the expression vector is a gamma retroviral vector.

20. The method of claim 17, wherein the tumor associated antigen is EGFR or HER2.

* * * * *

UNITED STATES PATENT AND TRADEMARK OFFICE
CERTIFICATE OF CORRECTION

PATENT NO. : 11,117,936 B2
APPLICATION NO. : 16/183579
DATED : September 14, 2021
INVENTOR(S) : Lohmueller It is certified that error appears in the above-identified patent and that said Letters Patent is hereby corrected as shown below:

On the Title Page

Item (73), "Assignee: University of Pittsburg – Of the Commonwealth System of Higher Education, Pittsburgh, PA (US)" should read -- Assignee: University of Pittsburgh – Of the Commonwealth System of Higher Education, Pittsburgh, PA (US) --

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*